(12) United States Patent
Masuno et al.

(10) Patent No.: US 10,010,493 B2
(45) Date of Patent: Jul. 3, 2018

(54) ESTER COMPOUND, AND COSMETIC COMPONENT AND COSMETIC PRODUCT EACH CONTAINING SAME

(71) Applicant: Kokyu Alcohol Kogyo Co., Ltd., Narita-shi, Chiba (JP)

(72) Inventors: Mari Masuno, Narita (JP); Kiyotaka Kawai, Narita (JP)

(73) Assignee: Kokyu Alcohol Kogyo Co., Ltd., Chiba (JP)

( * ) Notice: Subject to any disclaimer, the term of this patent is extended or adjusted under 35 U.S.C. 154(b) by 0 days.

(21) Appl. No.: 15/112,462

(22) PCT Filed: Jan. 19, 2015

(86) PCT No.: PCT/JP2015/051182
§ 371 (c)(1),
(2) Date: Jul. 19, 2016

(87) PCT Pub. No.: WO2015/108176
PCT Pub. Date: Jul. 23, 2015

(65) Prior Publication Data
US 2016/0331661 A1    Nov. 17, 2016

(30) Foreign Application Priority Data

Jan. 20, 2014 (JP) .................. 2014-007962
Jul. 8, 2014 (JP) .................. 2014-140768

(51) Int. Cl.
*A61K 8/37* (2006.01)
*A61Q 1/00* (2006.01)
(Continued)

(52) U.S. Cl.
CPC .................. *A61K 8/37* (2013.01); *A61Q 1/00* (2013.01); *A61Q 1/02* (2013.01); *A61Q 1/04* (2013.01);
(Continued)

(58) Field of Classification Search
None
See application file for complete search history.

(56) References Cited

U.S. PATENT DOCUMENTS 4,289,660 A    9/1981  Schaper et al.
4,411,828 A   10/1983  Fujikura et al.
(Continued)

FOREIGN PATENT DOCUMENTS

DE    934889      * 11/1955
DE    934889 C     11/1955
(Continued)

OTHER PUBLICATIONS

Mamedov (Catalytic Addition of Methacrylic Acid to Tricyclo[5.2.1.02,6]Deca-3,8-Diene and Some Transformations of the Resulting Ester. Neft Kimyasi va Neft E'mali Proseslari, 2008;(3-4):185-189—of record in the IDS filed on Oct. 27, 2016) and English abstract.*

(Continued)

*Primary Examiner* — Jafar Parsa
*Assistant Examiner* — Amy C Bonaparte
(74) *Attorney, Agent, or Firm* — Wolf, Greenfield & Sacks, P.C.

(57) ABSTRACT

The purpose of the present invention is to provide a novel ester compound which can be used as a component of a cosmetic component. An ester compound of tricyclo [5.2.1.0$^{2,6}$]decane, which is represented by formula (I).

20 Claims, 1 Drawing Sheet

(51) Int. Cl.
*A61Q 1/04* (2006.01)
*A61Q 1/06* (2006.01)
*A61Q 1/10* (2006.01)
*A61Q 5/00* (2006.01)
*A61Q 17/04* (2006.01)
*A61Q 19/00* (2006.01)
*A61Q 19/10* (2006.01)
*C07C 69/24* (2006.01)
*A61Q 1/02* (2006.01)
*A61Q 1/14* (2006.01)
*C07C 69/013* (2006.01)
*C07C 69/28* (2006.01)

(52) U.S. Cl.
CPC ............... *A61Q 1/06* (2013.01); *A61Q 1/10* (2013.01); *A61Q 1/14* (2013.01); *A61Q 5/00* (2013.01); *A61Q 17/04* (2013.01); *A61Q 19/00* (2013.01); *A61Q 19/007* (2013.01); *A61Q 19/10* (2013.01); *C07C 69/013* (2013.01); *C07C 69/24* (2013.01); *C07C 69/28* (2013.01); *A61K 2800/10* (2013.01); *A61K 2800/262* (2013.01); *A61K 2800/592* (2013.01); *C07C 2603/68* (2017.05)

(56) References Cited

U.S. PATENT DOCUMENTS

| | | | |
|---|---|---|---|
| 4,430,421 A | | 2/1984 | Van de Sande et al. |
| 6,387,398 B1 | * | 5/2002 | Vollhardt ............... A61K 8/046 424/401 |
| 2007/0155869 A1 | | 7/2007 | Dershem et al. |
| 2011/0009548 A1 | | 1/2011 | Dakka et al. |
| 2013/0187095 A1 | | 7/2013 | Dershem et al. |

FOREIGN PATENT DOCUMENTS

| | | |
|---|---|---|
| EP | 0 445 611 A1 | 9/1991 |
| FR | 2519630 A1 | 7/1983 |
| GB | 2019841 A | 11/1979 |
| JP | 55-027188 | 2/1980 |
| JP | 56-128735 | 10/1981 |
| JP | 58-121207 | 7/1983 |
| JP | 58-130337 | 8/1983 |
| JP | S6468745 * | 3/1989 |
| JP | 2004-062010 | 2/2004 |
| JP | 2005-206573 | 8/2005 |
| JP | 5580947 | 8/2014 |
| JP | 5663111 | 2/2015 |
| WO | WO 2011/005822 A1 | 1/2011 |

OTHER PUBLICATIONS

CID 44149086 (National Center for Biotechnology Information. PubChem Compound Database; CID=44149086, https://pubchem.ncbi.nlm.nih.gov/compound/44149086 (accessed Oct. 19, 2017)) (Year: 2017).*

SID 135196955 (National Center for Biotechnology Information. PubChem Substance Database; SID=135196955, https://pubchem.ncbi.nlm.nih.gov/substance/135196955; compound publicly available on Mar. 21, 2012 (accessed Oct. 19, 2017)) (Year: 2012).*

Supplementary European Search Report, dated Nov. 11, 2016, in connection with EP 15737191.5.

International Search Report and Written Opinion, dated Mar. 3, 2015, in connection with PCT/JP2015/051182.

International Preliminary Report on Patentability, dated Jul. 21, 2016, in connection with PCT/JP2015/051182.

Kleinpeter et al., Shifteffekte von Subatituenten unterschiedlicher Elektro-negativitat auf C-chemische Verschiebungen. Journal fuer Praktische Chemie. 1977;319(3):458-462.

Mamedov et al., Neft Kimyasi va Neft E'mali Proseslari. 2008;(3-4):185-189.

Mamedov et al., Catalytic Addition of Methacrylic Acid to Tricyclo[5.2.1.02,6]Deca-3,8-Diene and Some Transformations of the Resulting Ester. Neft Kimyasi va Neft E'mali Proseslari. 2008;(3-4):185-189.

* cited by examiner

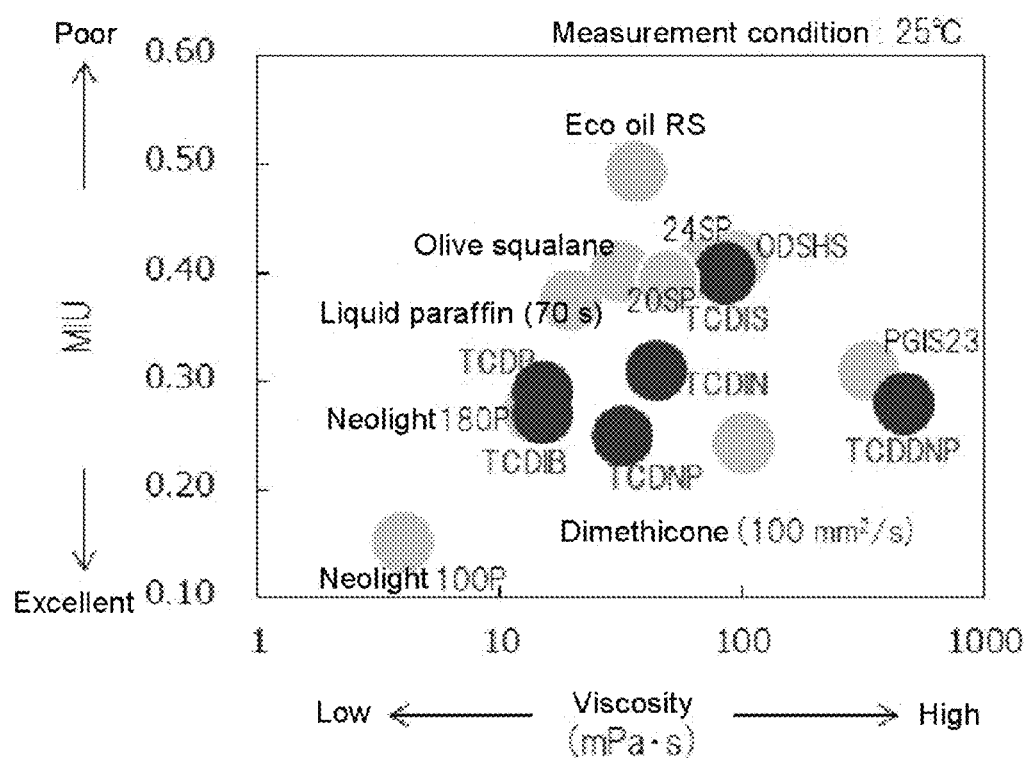

ESTER COMPOUND, AND COSMETIC COMPONENT AND COSMETIC PRODUCT EACH CONTAINING SAME

RELATED APPLICATION

This application is a national stage filing under 35 U.S.C. § 371 of international application PCT/JP2015/051182, filed Jan. 19, 2015, the disclosure of which is incorporated by reference herein in its entirety.

TECHNICAL FIELD

The present invention relates to an ester compound of tricyclo[$5.2.1.0^{2,6}$]decane, and a cosmetic material and a cosmetic product containing the same.

BACKGROUND ART

Conventionally, ester compounds have been known as components of cosmetic materials used in the manufacture of cosmetic products. These have been typically used as oil agents, etc. for cosmetic materials, as reported in, for example, Patent Document 1 wherein diester of saturated branched dihydric alcohols having a carbon number of 6-9 and neopentanoic acid is used as an oil agent for cosmetic materials (cosmetic products). Meanwhile, in the areas other than cosmetic materials, for example, an ester of tricyclo[$5.2.1.0^{2,6}$]decane-2-methylol is known as a fragrance (Patent Documents 2-4), and a compound having a structure of tricyclo[$5.2.1.0^{2,6}$]decane ester is known as a compound used in a thermosetting adhesive compositions (Patent Documents 5 and 6).

PRIOR ART DOCUMENTS

Patent Documents

Patent Document 1: JP A No. 2005-206573
Patent Document 2: JP A S55-27188
Patent Document 3: JP A S56-128735
Patent Document 4: JP A 58-121207
Patent Document 5: US 2007/0155869 A1
Patent Document 6: US 2013/0187095 A1

SUMMARY OF THE INVENTION

Problems to be Solved by the Invention

Despite the presence of a variety of ester compounds as one of cosmetic materials used in the manufacture of cosmetic products, needs for diversifying new cosmetic products are continuously increasing, and existing cosmetic ester compounds are not sufficient to meet all such needs. For example, conventional ester compounds induce sweating in solid cosmetic products and they cannot be used for certain types of cosmetic products, causing a situation of unsatisfied needs. Based on the recognition that it is extremely important to prepare ester compounds having various physical properties in order to meet a variety of needs as a cosmetic material, the present inventors intend to provide a series of components of cosmetic materials that can correspond to a variety of needs; and by searching new ester compounds that can be used as a component of cosmetic materials, the inventors have worked on the research with an object of providing components of cosmetic materials that contribute to the manufacture of cosmetic products having excellent properties.

In skin care and body care products, low viscosity oils are preferred by consumers due to their light feeling of use, but they exhibit poor moisturizing feeling (moisturized feeling). In contrast, when moisturizing feeling (moisturized feeling) is desired, high viscosity oils may be blended; however, tackiness may be felt and there is a tendency of texture deterioration. Therefore, a raw material capable of providing light feeling of use as well as some degree of moisturized feeling in use is required.

In addition, in cleansing formulation, although light oil agents dissolve makeup well, they tend to show strong dry feeling and tensioned skin after washing. Therefore, an oil agent dissolving makeup well without causing tensioned skin after washing (with appropriate moisturized feeling) is desired.

Furthermore, in hair care products, for the care for damages caused by perm and coloring and damages caused by day-to-day ultraviolet light, as hair treatment products, various types of in-bath products (conditioners, hair packs, regular (i.e., rinsed-out type) treatments) and out-bus products (hair oils, leave-in treatments) are put on the market. In hair care products such as hair oils as well, a product with non-tacky feeling at the time of application, providing finger-combing smoothness (good finger combability) after application (no feeling of roughness) and good hair manageability without tackiness is desired.

Means for Solving the Problems

While conducting extensive research to solve the above problems, the present inventors have focused on an ester compound of tricyclo[$5.2.1.0^{2,6}$]decane that had not yet been focused as a component of cosmetic materials before, and found that this compound has various excellent properties as a component of cosmetic materials; as a result of further research, the present inventors have completed the present invention.

Namely, the present invention relates to the following [C1]-[C19].

[C1]

A compound of formula (I):

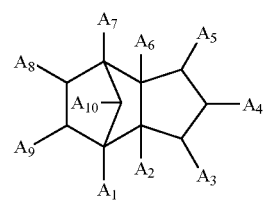

(I)

wherein
$A_1$-$A_{10}$ are, each independently of one another, H or R—X—Y—,
wherein
R is a C6-C22 linear or branched alkyl group,
X is —CO—O— or —O—CO—,
Y is a single bond or —CH$_2$—,
at least one of $A_1$-$A_{10}$ is R—X—Y—,
when a plurality of R—X—Y— are present, each of R, X, Y is independently selected.

[C2]

A compound of formula (Ia-1):

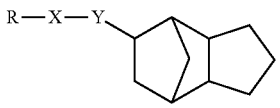

wherein
R is a C4-C22 linear or branched alkyl group,
X is —CO—O— or —O—CO—,
Y is a single bond or —CH$_2$—,
wherein, when R is a C4 linear or branched alkyl group, Y is —CH$_2$—.
[C3]
A compound of formula (Ia-2):

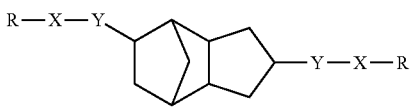

wherein
R is a C3-C22 linear or branched alkyl group,
X is —CO—O— or —O—CO—,
Y is a single bond or —CH$_2$—,
each of R, X and Y is independently selected.
[C4]
A cosmetic material comprising a compound of formula (I) (excluding a fragrance):

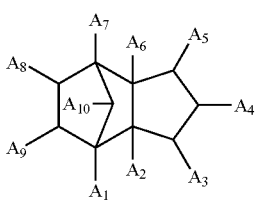

wherein
A$_1$-A$_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of A$_1$-A$_{10}$ is R—X—Y—,
when a plurality of R—X—Y— are present, each of R, X, Y is independently selected.
[C5]
A cosmetic material comprising a compound of formula (Ia-1):

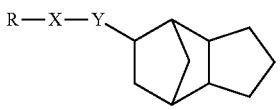

wherein
R is a C3-C22 linear or branched alkyl group,
X is —CO—O— or —O—CO—,
Y is a single bond or —CH$_2$—.
[C6]
A cosmetic material comprising a compound of formula (Ia-2):

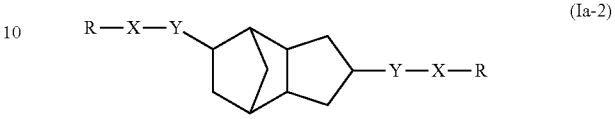

wherein
R is a C3-C22 linear or branched alkyl group,
X is —CO—O— or —O—CO—,
Y is a single bond or —CH$_2$—,
each of R, X and Y is independently selected.
[C7]
A cosmetic product comprising the cosmetic material according to any one of [C4] to [C6].
[C8]
The cosmetic product according to [C7], which is a lip rouge or lip gloss.
[C9]
An agent for improving feeling of use of cosmetic products, comprising a compound of formula (I):

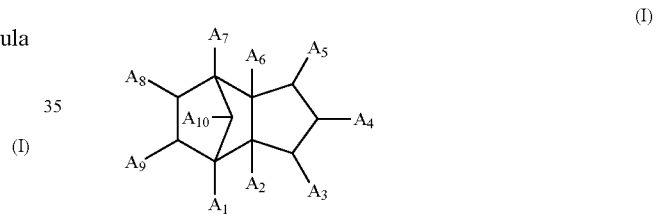

wherein
A$_1$-A$_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of A$_1$-A$_{10}$ is R—X—Y—,
when a plurality of R—X—Y— are present, each of R, X, Y is independently selected.
[C10]
An agent for improving feeling of use cosmetic products, comprising a compound of formula (Ia):

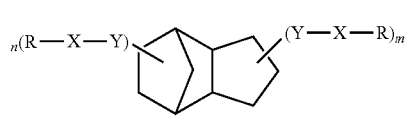

wherein
n and m are, each independently, 0, 1 or 2,
n+m is 1, 2 or 3,
R is a C3-C22 linear or branched alkyl group,
X is —CO—O— or —O—CO—,
Y is a single bond or —CH$_2$—, when a plurality of R—X—Y— are present, each of R, X, Y is independently selected.

[C11]

An agent for improving feeling of use of cosmetic products, comprising a compound of formula (Ia-1):

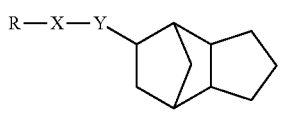
(Ia-1)

wherein
R is a C3-C22 linear or branched alkyl group,
X is —CO—O— or —O—CO—,
Y is a single bond or —CH$_2$—.

[C12]

An agent for improving feeling of use of cosmetic products, comprising a compound of formula (Ia-2):

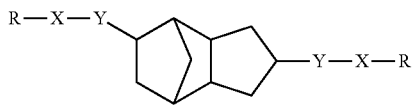
(Ia-2)

wherein
R is a C3-C22 linear or branched alkyl group,
X is —CO—O— or —O—CO—,
Y is a single bond or —CH$_2$—,
each of R, X, Y is independently selected.

[C13]

The agent for improving feeling of use according to any one of [C9] to [C12], wherein the cosmetic product is a hair care product, a skin care product, a body care product and/or a make-up product.

[C14]

The agent for improving feeling of use according to [C13], wherein the skin care product is a cleansing product.

[C15]

A cosmetic product comprising a compound of formula (I):

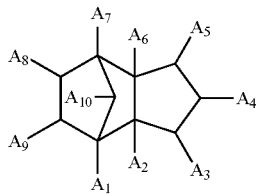
(I)

wherein
$A_1$-$A_{10}$ are, each independently of one another, H or R—X—Y—,
wherein
R is a C6-C22 linear or branched alkyl group,
X is —CO—O— or —O—CO—,
Y is a single bond or —CH$_2$—,
at least one of $A_1$-$A_{10}$ is R—X—Y—,
when a plurality of R—X—Y— are present, each of R, X, Y is independently selected.

[C16]

The cosmetic product according to [C15], which is selected from the group consisting of make-up products, hair care products, skin care products, and body care products.

[C17]

Use of a compound of formula (I) as an agent for improving feeling of use of cosmetic products:

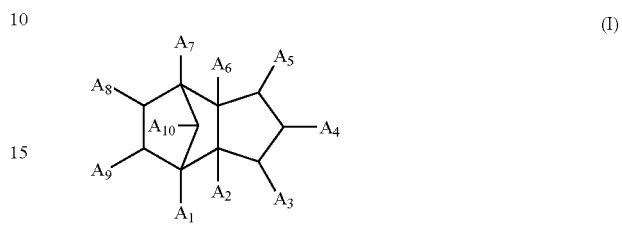
(I)

wherein
$A_1$-$A_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of $A_1$-$A_{10}$ is R—X—Y—,
when a plurality of R—X—Y— are present, each of R, X, Y is independently selected.

[C18]

Use of a compound of formula (I) as a cosmetic material:

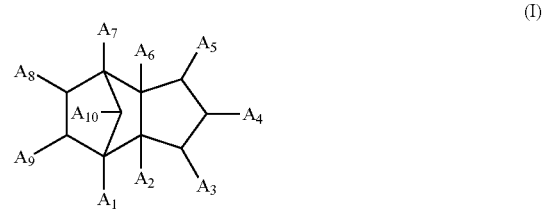
(I)

wherein
$A_1$-$A_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of $A_1$-$A_{10}$ is R—X—Y—,
when a plurality of R—X—Y— are present, each of R, X, Y is independently selected.

Furthermore, the present invention relates to the following [1]-[9].

[1]

A cosmetic material (excluding a fragrance) for make-up products, hair care products, skin care products and/or body care products, comprising a compound of formula (I):

(I)

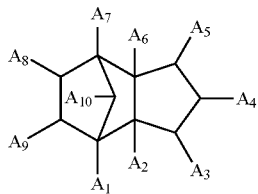

wherein
$A_1$-$A_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of $A_1$-$A_{10}$ is R—X—Y—,
when a plurality of R—X—Y— are present, each of R, X, Y is independently selected.

[2]
A cosmetic material for make-up products, hair care products, skin care products and/or body care products, comprising a compound of formula (Ia):

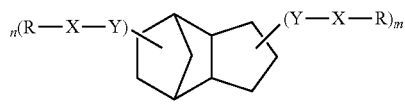
(Ia)

wherein
n and m are, each independently, 0, 1 or 2,
n+m is 1, 2 or 3,
R is a C3-C22 linear or branched alkyl group,
X is —CO—O— or —O—CO—,
Y is a single bond or —CH$_2$—,
when a plurality of R—X—Y— are present, each of R, X, Y is independently selected.

[3]
A cosmetic material for make-up products, hair care products, skin care products and/or body care products, comprising a compound of formula (Ia-1):

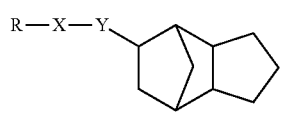
(Ia-1)

wherein
R is a C3-C22 linear or branched alkyl group,
X is —CO—O— or —O—CO—,
Y is a single bond or —CH$_2$—.

[4]
A cosmetic material for make-up products, hair care products, skin care products and/or body care products, comprising a compound of formula (Ia-2):

[Formula 17]

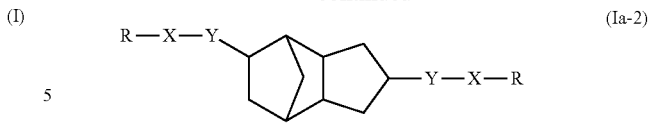
(Ia-2)

wherein
R is a C3-C22 linear or branched alkyl group,
X is —CO—O— or —O—CO—,
Y is a single bond or —CH$_2$—,
each of R, X, Y is independently selected.

[5]
A hair care product, a skin care product and/or a body care product, comprising a cosmetic material according to any one of [1] to [4].

[6]
The skin care product according to [5], which is a skin care product.

[7]
A texture improving agent comprising a compound of formula (I):

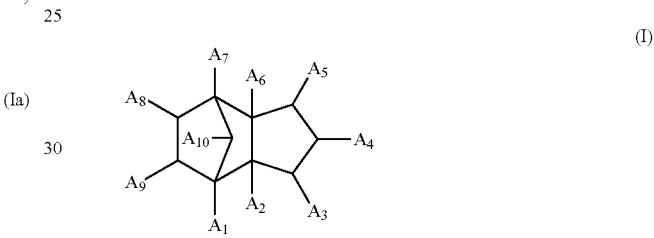
(I)

wherein
$A_1$-$A_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of $A_1$-$A_{10}$ is R—X—Y—,
when a plurality of R—X—Y— are present, each of R, X, Y is independently selected.

[8]
A cosmetic product comprising the texture improving agent according to [7].

[9]
A method for improving the texture of cosmetic products, comprising adding a compound of formula (I):

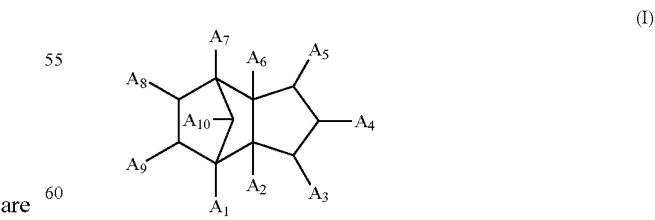
(I)

wherein
$A_1$-$A_{10}$ are, each independently of one another, H or R—X—Y—,
wherein
R is a C3-C22 linear or branched alkyl group, X is —CO—O— or —O—CO—,
Y is a single bond or —CH$_2$—,
at least one of A$_1$-A$_{10}$ is R—X—Y—,
when a plurality of R—X—Y— are present, each of R, X, Y is independently selected.

Furthermore, the present invention relates to the following (1) to (3).

(1)
A compound of formula (I):

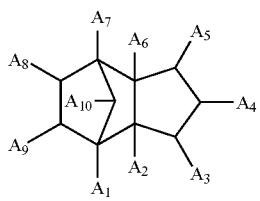

(I)

wherein
A$_1$-A$_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of A$_1$-A$_{10}$ is R—X—Y—,
when a plurality of R—X—Y— are present, each of R, X, Y is independently selected,
provided that when only A$_2$ or A$_6$ is R—X—Y—, X is —O—CO—, and Y is —CH$_2$—, then R is not a C3 linear or branched alkyl group.

(2)
A cosmetic material comprising a compound of formula (I):

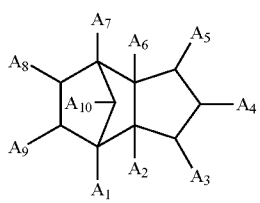

(I)

wherein
A$_1$-A$_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of A$_1$-A$_{10}$ is R—X—Y—,
when a plurality of R—X—Y— are present, each of R, X, Y is independently selected.

(3)
A cosmetic product comprising the cosmetic material according to (2).

Advantageous Effects of the Invention

The present invention provides novel ester compounds which can be used in a variety of cosmetic products; for example, in solid cosmetic products such as lipsticks, said compounds give storage stability (prevention of sweating), good feeling of use such as smoothness, as well as functionality such as glossiness and adhesion; in milky or liquid cosmetic products such as shampoo and skin lotion, they give good feeling of use such as smooth texture, adhesiveness, and moisturized feeling; furthermore, in cleansing preparations, they improve cleansing power; in emulsions such as skin cream, massage cream and hair treatment, they improve the touch during use.

In addition, the present invention provides cosmetic products with excellent feeling of use (smoothness during use, moisturized feeling after use, and non-tacky feeling after use) by using the novel ester compounds.

BRIEF DESCRIPTION OF DRAWINGS

The FIGURE is a diagram showing the relationship between viscosity and smoothness of ester compounds.

MODES FOR CARRYING OUT THE INVENTION

A compound of formula (I) is represented by the following formula (I):

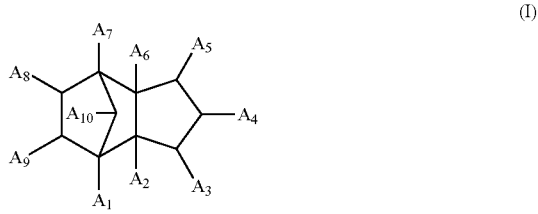

(I)

wherein
A$_1$-A$_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of A$_1$-A$_{10}$ is R—X—Y—,
when a plurality of R—X—Y— are present, each of R, X, Y is independently selected.

However, in one embodiment of the present invention, when only A$_2$ or A$_6$ is R—X—Y—, X is —O—CO—, and Y is —CH$_2$—, then R is not a C3 linear or branched alkyl group.

In addition, in one embodiment of the present invention, when only A$_3$, A$_4$ or A$_5$ is R—X—Y—, X is —O—CO—, and Y is a single bond or —CH$_2$—, then R is not a C3-C5 linear or branched alkyl group.

Furthermore, in one embodiment of the present invention, when only A$_2$ or A$_6$ is R—X—Y—, X is —O—CO—, and Y is a single bond, then R is not a C3 linear or branched alkyl group.

In one embodiment of the present invention, from one to four, preferably from one to three, more preferably one or two A$_1$-A$_{10}$ is/are R—X—Y—, and the remaining A$_1$-A$_{10}$ are H.

In one embodiment of the present invention, it is preferred that A$_2$ and A$_6$ are H.

In one embodiment of the present invention, it is preferred that A$_1$, A$_2$, A$_6$ and A$_7$ are H.

In one embodiment of the present invention, it is preferred that one or both of $A_8$ and $A_{10}$ is/are R—X—Y—, and the remaining $A_1$-$A_{10}$ are H.

In one embodiment of the present invention, it is preferred that one or two of $A_3$-$A_5$ is/are R—X—Y—, and the remaining $A_1$-$A_{10}$ are H.

In one embodiment of the present invention, it is preferred that one of $A_8$ and $A_{10}$ and one of $A_3$-$A_5$ are R—X—Y—, and the remaining $A_1$-$A_{10}$ are H.

Here, in the above formula (I), when the same symbol appears more than once, for each such symbol in each occurrence, a definition for each symbol is independently selected. That is, a plurality of identical symbols appearing in formula (I) may be the same or different. The same applies in the general formulae of other compounds described herein.

Among the ester compounds represented by the above formula (I), the compound represented by the following formula (Ia) is preferred:

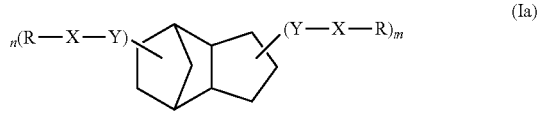

wherein
n and m are, each independently, 0, 1 or 2,
n+m is 1, 2 or 3,
R is a C3-C22 linear or branched alkyl group,
X is —CO—O— or —O—CO—,
Y is a single bond or —CH$_2$—,
when a plurality of R—X—Y— are present, each of R, X, Y is independently selected.

Among the ester compounds represented by the above formula (Ia), the compound of formula (Ia-1):

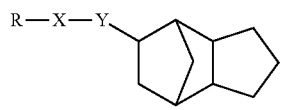

wherein
R is a C3-C22 linear or branched alkyl group,
X is —CO—O— or —O—CO—,
Y is a single bond or —CH$_2$—; and
the compound of formula (Ia-2):

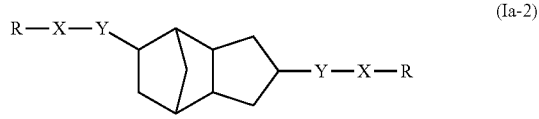

wherein
R is a C3-C22 linear or branched alkyl group,
X is —CO—O— or —O—CO—,
Y is a single bond or —CH$_2$—,
each of R, X and Y is independently selected;
are preferred.

In the above formulae, when a plurality of R are present, they may be the same or different, but a plurality of R are preferably the same.

In one embodiment of the present invention, from the viewpoint of odor, it is preferred that R is C4-C22.

Examples of R specifically include, but are not limited to, n-propyl, isopropyl, n-butyl, isobutyl, sec-butyl, tert-butyl, n-pentyl, isopentyl, neopentyl, ethylhexyl, isononyl, isostearyl, behenyl, etc.

In one embodiment of the present invention, R is a C4-C22, preferably C4-C18, and more preferably C5-C18 linear or branched alkyl group.

In one embodiment of the present invention, in the above formulae, it is preferred that:
when X is —O—CO—, then Y is —CH$_2$—, and,
when X is —CO—O—, then Y is a single bond.

<Method of Producing the Compound of Formula (I)>

An ester compound of tricyclo[5.2.1.0$^{2,6}$]decane (hereinafter, also referred to as "TCD ester") can be produced using a known method for producing esters.

For example, it can be produced by esterification reaction of tricyclo[5.2.1.0$^{2,6}$]decane alcohol with C4-C22 linear or branched saturated fatty acid.

Alternatively, it can be produced by esterification reaction of tricyclo[5.2.1.0$^{2,6}$]decanoic acid with C3-C22 linear or branched saturated fatty acid alcohol.

<Cosmetic Material>

The cosmetic material of the present invention comprises a compound represented by the following formula (I):

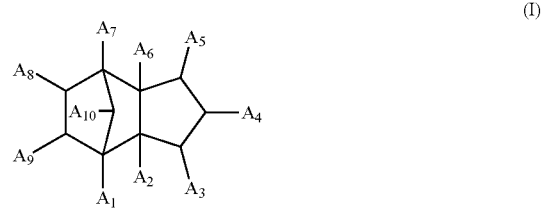

wherein
$A_1$-$A_{10}$ are, each independently of one another, H or R—X—Y—,
wherein
R is a C3-C22 linear or branched alkyl group,
X is —CO—O— or —O—CO—,
Y is a single bond or —CH$_2$—,
at least one of $A_1$-$A_{10}$ is R—X—Y—,
when a plurality of R—X—Y— are present, each of R, X, Y is independently selected.

In one embodiment of the present invention, in the above formula (I), when only $A_2$ or $A_6$ is R—X—Y—, X is —O—CO—, and Y is —CH$_2$—, then R is not a C3 linear or branched alkyl group.

In one embodiment of the present invention, in the above formula (I), from the viewpoint of odor, R is preferably a C4-C22 linear or branched alkyl group.

In one embodiment of the present invention, the cosmetic material comprises at least one of the compounds represented by the above formula (Ia).

In one embodiment of the present invention, the cosmetic material comprises at least one of the compounds represented by the above formula (Ia-1).

In one embodiment of the present invention, the cosmetic material comprises at least one of the compounds represented by the above formula (Ia-2).

In a preferred embodiment of the present invention, the cosmetic material comprises at least one of the compounds represented by the above formulae.

"Cosmetic material" as used herein includes a component (base material) that provides basic shape and performance to cosmetic products, for example oil agents and the like; however, in a preferred embodiment of the present invention, additives such as fragrance that provide additional functions are not encompassed in the cosmetic material.

"Cosmetic material" as used herein may be a composition comprising, in addition to the compound of formula (I), other components of cosmetic material normally used to provide a particular shape to cosmetic products.

Examples of other components of cosmetic material include, but are not limited to, solid fat and oil, liquid oil, silicone oil, silicone derivatives, gelling agent, thickening agent, surfactant, water, etc.

In one embodiment of the present invention, a cosmetic material may consist of only the compounds of formula (I), or may comprise other components of cosmetic material.

In a preferred embodiment of the present invention, the cosmetic material is a composition comprising, in addition to at least one of the ester compounds represented by the above formulae, other components of cosmetic material that are preferably simultaneously used.

The cosmetic material may be used for producing various cosmetic products.

In one embodiment of the present invention, preferably, the cosmetic material is used for producing make-up products, in particular solid, semi-solid, and liquid make-up cosmetic products.

In one embodiment of the present invention, preferably, the cosmetic material is used for producing hair care products, skin care products, and/or body care products.

In one embodiment of the present invention, the cosmetic material comprises a gelling agent, in addition to the compound of formula (I). For example, in the production of transparent solid cosmetic products, examples of gelling agent include, but are not limited to, amino acid-based oil gelling agents such as dibutyl lauroyl glutamide and dibutyl ethylhexanoyl glutamide, polyamide resins such as ethylenediamine/stearyl dimer dilinoleate) copolymer (trade name: UNICLEAR™ 100VG), bisdialkyl(C14-18)amide (ethylenediamine/hydrogenated dimer dilinoleate) copolymer (trade name: SYLVACLEAR™ A200V).

"Cosmetic product" as used herein is not particularly limited, but it means any product which is applied to the skin, hair, and lip, etc. for the purpose of cleaning the body or improving the appearance. Specifically, it includes, but is not limited to, skin care products, make-up products, hair care products, and body care products.

Examples of skin care products include, but are not limited to, skin lotions, creams, skin milks, gels, beauty essences, cosmetic oils, packs, cleansings, facial cleansers, whitening cosmetics, UV care cosmetics, etc.

Examples of make-up products include, but are not limited to, foundation primers, foundations, lip colors, lipsticks, lip balms, lip glosses, cheek colors, eyeliners, mascaras, eye shadows, eyebrows, etc.

Examples of hair care products include, but are not limited to, shampoos, conditioners, hair rinses, hair treatments, hair stylings, perming agents, hair colors, etc.

Examples of body care products include, but are not limited to, body shampoos, body lotions, hand creams, nail creams, deodorant cosmetics, etc.

Since the compound of formula (I) is highly compatible with oil agents, it is suitable for use in cosmetic products containing oil agents.

Since the compound of formula (I) has high smoothness, it is suitable for use in skin care products, make-up products, in particular lip rouges and lip glosses, and in body care products.

Since the compound of formula (I) has light feeling of use as well as moisturized feeling of use, it is suitable for use in cosmetic products that are applied by spreading on the skin, hair and lip, etc., in particular cosmetic products wherein moisture retention is desired, such as skin care products, body care products, and hair care products.

Since the compound of formula (I) is highly compatible with oils and has moisturized feeling of use, it is suitable for use in cleansing products, for example, cleansing oils, cleansing milks, cleansing gels, cleansing liquids, cleansing creams, and point make-up removers.

The shape of cosmetic products is not particularly limited, and it may be solid, liquid, emulsion, cream, and gel.

Since the compound of formula (I) has high smoothness, it is suitable for use in all cosmetic products for application to the lip, skin, and hair, etc. In one embodiment of the present invention, it is also possible to use the compound of formula (I) as a smoothness improver for cosmetic products.

Since the compound of formula (I) has excellent texture-improving property, it is suitable for use in all cosmetic products for application to the lip, skin, and hair, etc. In one embodiment of the present invention, it is also possible to use the compound of formula (I) as a texture improving agent for cosmetic products.

Since the compound of formula (I) has excellent storage stability (prevention of sweating), it is suitable for use in solid cosmetic products.

The amount of an ester compound represented by the above formulae in a cosmetic product differs depending on the type of cosmetic product of interest and other materials to be combined, and it may be adjusted as appropriate by those skilled in the art.

In one embodiment of the present invention, a cosmetic product comprises an ester compound of the above formulae at 0.1-90 wt %, preferably 2-50 wt %, and more preferably 10-30 wt %.

When the cosmetic product is a make-up product, the make-up product comprises an ester compound represented by the above formulae at 2-80 wt %, preferably 5-75 wt %, and more preferably 10-70 wt %.

When the cosmetic product is a lip rouge, the lip rouge comprises an ester compound of the above formulae at 5 wt % or more, preferably 10 wt % or more, and more preferably 15 wt % or more.

When the cosmetic product is a solid type, in particular a stick type, it comprises an ester compound of the above formulae at 5-50 wt %, and preferably 10-30 wt %.

When the cosmetic product is a hair care product, the hair care product comprises an ester compound of the above formulae at 1-90 wt %, preferably 5-80 wt %, and more preferably 10-70 wt %.

When the cosmetic product is a hair oil, hair cream or hair styling agent, the hair oil, hair cream or hair styling agent comprises an ester compound of the above formulae at 1-80 wt %, preferably 3-70 wt %, and more preferably 5-60 wt %.

When the cosmetic product is a skin care product, the skin care product comprises an ester compound of the above formulae at 0.1-90 wt %, preferably 0.5-85 wt %, and more preferably 1.0-75 wt %.

When the cosmetic product is a skin cream, cosmetic oil or UV care cosmetics, the skin cream, cosmetic oil or UV care cosmetics comprises an ester compound of the above formulae at 0.1-70 wt %, preferably 0.5-60 wt %, and more preferably 1-50 wt %.

When the cosmetic product is a cleanser, the cleanser comprises an ester compound of the above formulae at 0.1-80 wt %, preferably 0.5-75 wt %, and more preferably 1-70 wt %.

When the cosmetic product is a body care product, the body care product comprises an ester compound of the above formulae at 0.1-70 wt %, preferably 0.5-60 wt %, and more preferably 1-50 wt %.

When the cosmetic product is an oil-based cosmetic product, the oil-based cosmetic product comprises an ester compound of the above formulae at 1-90 wt %, preferably 3-85 wt %, and more preferably 5-75 wt %.

When the cosmetic product is a cream-type cosmetic product, the cream-type cosmetic product comprises an ester compound of the above formulae at 0.1-80 wt %, preferably 0.5-75 wt %, and more preferably 1-70 wt %.

Cosmetic products can be produced by known method for producing cosmetic products. For example, components of cosmetic materials are dissolved with stirring to obtain a homogeneous mixture, to which additives such as fragrance are added, then the mixture is molded to obtain a cosmetic product.

In one embodiment of the present invention, a method for producing a cosmetic product, comprising adding an ester compound of the present invention, is provided.

In one embodiment of the present invention, it is possible to improve the texture of cosmetic products by adding the ester compound of the present invention. In a preferred embodiment of the present invention, a smooth texture (feeling of use/feeling of application) is provided to cosmetic products by adding the ester compound of the present invention.

Accordingly, in one embodiment of the present invention, a method for improving the texture of cosmetic products, comprising adding the ester compound of the present invention, is provided.

From the viewpoint of smoothness, the ester compounds of the present invention have a mean frictional coefficient (MIU) of 0-0.5, preferably 0-0.4. From the viewpoint of non-roughness, they have a fluctuation of mean frictional coefficient (MMD) of 0-0.010, preferably 0-0.008.

From the viewpoint of providing a light texture, the ester compounds of the present invention have a viscosity of 0-600, preferably 10-500.

Hereinafter, the present invention will be described in more detail based on examples; however, the present invention is not limited to these examples, and various modifications are possible without departing from the technical idea of the present invention. As used herein, unless explicitly specified otherwise, % means wt %.

EXAMPLES

Synthesis Example 1

Synthesis of tricyclo[5.2.1.0$^{2,6}$]deca-8-yl-methyl neopentanoate 840 g of 8-hydroxymethyl-tricyclo[5.2.1.0$^{2,6}$]decane (product name: TCD-Alcohol M, supplier: Oxea Corporation) and a sufficient amount of neopentanoic acid were dissolved in toluene, to which an acid catalyst was added, and the mixture was heated to reflux and subjected to conventional esterification reaction to obtain 1200 g of a colorless liquid (95% yield, 99.7% purity).

Synthesis Example 2

Synthesis of tricyclo[5.2.1.0$^{2,6}$]deca-8-yl-methyl-n-pentanoate

Except that n-pentanoic acid was used in place of neopentanoic acid in Synthesis Example 1, the same reaction as in Synthesis Example 1 was carried out to obtain 1162 g of a colorless liquid (92% yield, 99.2% purity).

Synthesis Example 3

Synthesis of tricyclo[5.2.1.0$^{2,6}$]deca-8-yl-methyl isobutanoate

Except that isobutanoic acid was used in place of neopentanoic acid in Synthesis Example 1, the same reaction as in Synthesis Example 1 was carried out to obtain 1075 g of a colorless liquid (90% yield, 99.3% purity).

Synthesis Example 4

Synthesis of tricyclo[5.2.1.0$^{2,6}$]deca-8-yl-methyl isononanoate

Except that isononanoic acid was used in place of neopentanoic acid in Synthesis Example 1, the same reaction as in Synthesis Example 1 was carried out to obtain 1455 g of a colorless liquid (94% yield, 99.6% purity).

Synthesis Example 5

Synthesis of tricyclo[5.2.1.0$^{2,6}$]deca-8-yl-methyl isostearate

Except that isostearic acid was used in place of neopentanoic acid in Synthesis Example 1, the same reaction as in Synthesis Example 1 was carried out to obtain 2076 g of a colorless liquid (95% yield, 99.7% purity).

Synthesis Example 6

Synthesis of tricyclo[5.2.1.0$^{2,6}$]deca-8-yl-methyl behenate

Except that behenic acid is used in place of neopentanoic acid in Synthesis Example 1, the same reaction as in Synthesis Example 1 is carried out to obtain the product.

Synthesis Example 7

Synthesis of tricyclo[5.2.1.0$^{2,6}$]deca-8-yl-methyl-2-ethyl hexanoate

Except that 2-ethylhexanoic acid is used in place of neopentanoic acid in Synthesis Example 1, the same reaction as in Synthesis Example 1 is carried out to obtain the product.

Synthesis Example 8

Synthesis of 3,8-bis-(neopentanoyloxymethyl)-tricyclo[5.2.1.0$^{2,6}$]decane 840 g of 3,8-bis-(hydroxymethyl)-tricyclo[5.2.1.0$^{2,6}$]decane (CAS: 26896-48-0, product name: TCD-Alcohol DM, supplier: Oxea Corporation) and a sufficient amount of neopentanoic acid were dissolved in toluene, to which an acid catalyst was added, and the mixture was heated to reflux and subjected to conventional esterification reaction to obtain 1420 g of a colorless liquid (91% yield, 99.4% purity).

Synthesis Example A

Synthesis of tricyclo[5.2.1.0$^{2,6}$]deca-8-yl-methyl acetate 50 g of 8-hydroxymethyl-tricyclo[5.2.1.0$^{2,6}$]decane (product name: TCD-Alcohol M, supplier: Oxea Corporation) and 50 g of a mixture of acetic anhydride and pyridine (molar ratio 1:1) were refluxed at 95-100° C. and subjected to conventional esterification reaction to obtain 60 g of a colorless liquid (95% yield, 99.5% purity).

Physical properties of the ester compounds obtained in Synthesis Examples 1 to 5 and 8 are shown below.

In the present specification, each of the tricyclo[5.2.1.0$^{2,6}$]decane ester compounds is represented using the following abbreviations.
Synthesis Example 1: TCDNP: Ester of neopentanoic acid and TCD-Alcohol M
Synthesis Example 2: TCDP: Ester of n-pentanoic acid and TCD-Alcohol M
Synthesis Example 3: TCDIB: Ester of isobutanoic acid and TCD-Alcohol M
Synthesis Example 4: TCDIN: Ester of isononanoic acid and TCD-Alcohol M
Synthesis Example 5: TCDIS: Ester of isostearic acid and TCD-Alcohol M
Synthesis Example 8: TCDDNP: Diester of neopentanoic acid and TCD-Alcohol DM <Glossiness (Refractive Index)>

Measurement is carried out using Abbe refractometer NTR-2T (Atago Co., Ltd.) at 20° C., and resulting values represent refractive index.

Smoothness of ester compounds was measured using KES-SE Friction Tester (Kato Tech Co., Ltd.) with a detection-unit jig (an accessory of the tester, made of silicone rubber with irregularities resembling a human finger) and artificial leather (artificial leather Supplare produced by Idemitsu Technofine Co., Ltd.). On the artificial leather, 0.1 ml of an ester compound was droped. The jig was contacted to the site on the surface of the artificial leather where the oil agent was dropped. Temperature of the leather, oil agent and jig was adjusted to 25° C. in a constant temperature bath. Then, the jig was moved back and forth once at the same site with a speed of 1 mm/s (the moving distance of the jig was approximately 80 mm in one back-and-forth movement), and a mean frictional coefficient (MIU) and a fluctuation of mean frictional coefficient (MMD) for one back-and-forth movement were measured. The measurement was performed three times and the average values of MIU and MMD were calculated, which were used as indices of smoothness. For comparison, MIU and MMD of the various ester compounds used in the viscosity measurement were also measured.

Results are shown in Table 2.

TABLE 2

Viscosity and smoothness (MIU and MMD) of ester compounds.

| Component | Viscosity (mPa · s, 25° C.) | MIU | MMD |
| --- | --- | --- | --- |
| Isodecyl neopentanoate | 4 | 0.15 | 0.005 |
| Isostearyl neopentanoate | 14 | 0.27 | 0.006 |
| TCD ester of Synthesis Ex. 2 (TCDP) | 15 | 0.29 | 0.005 |
| TCD ester of Synthesis Ex. 3 (TCDIB) | 15 | 0.27 | 0.005 |
| Mineral oil | 20 | 0.37 | 0.007 |
| Squalane | 32 | 0.40 | 0.007 |
| TCD ester of Synthesis Ex. 1 (TCDNP) | 32 | 0.25 | 0.006 |
| Jojoba seed oil | 37 | 0.49 | 0.007 |
| TCD ester of Synthesis Ex. 4 | 44 | 0.31 | 0.006 |

TABLE 1

Refractive index of ester compounds.

| | Synthesis Ex. 1 TCDNP | Synthesis Ex. 2 TCDP | Synthesis Ex. 3 TCDIB | Synthesis Ex. 4 TCDIN | Synthesis Ex. 5 TCDIS | Synthesis Ex. 8 TCDDNP |
| --- | --- | --- | --- | --- | --- | --- |
| Refractive index | 1.479 | 1.484 | 1.483 | 1.479 | 1.482 | 1.472 |

| | Isodecyl neopentanoate | Isotridecyl isononanoate | Isostearyl neopentanoate | Mineral oil | Pentaerythrityl tetraisostearate | Hydrogenated polyisobutene | Lanolin |
| --- | --- | --- | --- | --- | --- | --- | --- |
| Refractive index | 1.430 | 1.445 | 1.446 | 1.464 | 1.468 | 1.494 | 1.496 |

Isodecyl neopentanoate: trade name NEOLIGHT 100P (Supplier: Kokyu Alcohol Kogyo Co., Ltd.)
Isotridecyl isononanoate: trade name KAK139 (Supplier: Kokyu Alcohol Kogyo Co., Ltd.)
Isostearyl neopentanoate: trade name NEOLIGHT 180P (Supplier: Kokyu Alcohol Kogyo Co., Ltd.)
Pentaerythrityl tetraisostearate: trade name KAK PTI (Supplier: Kokyu Alcohol Kogyo Co., Ltd.)

As shown in Table 1, the compounds of formula (I) have a higher refractive index compared to esters commonly used in cosmetic products. Therefore, the compounds of formula (I) are suitable for use in cosmetic products wherein glossiness is required.

<Viscosity, Smoothness>

Viscosity of ester compounds was measured using Brookfield viscometer DV-II+ (spindle No. 2, 12 rpm, 25° C.). As a comparison, viscosity of oil agents commonly used in cosmetic products was also measured.

TABLE 2-continued

Viscosity and smoothness (MIU and MMD) of ester compounds.

| Component | Viscosity (mPa · s, 25° C.) | MIU | MMD |
| --- | --- | --- | --- |
| (TCDIN) | | | |
| Octyldodecanol | 49 | 0.39 | 0.007 |
| Decyldodecanol | 69 | 0.40 | 0.006 |

TABLE 2-continued

Viscosity and smoothness (MIU and MMD) of ester compounds.

| Component | Viscosity (mPa · s, 25° C.) | MIU | MMD |
|---|---|---|---|
| TCD ester of Synthesis Ex. 5 (TCDIS) | 85 | 0.40 | 0.006 |
| Octyldodecyl stearoyloxy stearate | 96 | 0.41 | 0.006 |
| Dimethicone | 103 | 0.24 | 0.007 |
| Polyglyceryl-2 triisostearate | 339 | 0.31 | 0.008 |
| TCD ester of Synthesis Ex. 8 (TCDDNP) | 462 | 0.28 | 0.006 |

The relationship between viscosity and smoothness (MIU) is shown in FIG. 1.

TCDNP and TCDIN have superior smoothness than squalane (trade name: OLIVE SQUALANE, Supplier: Kokyu Alcohol Kogyo Co., Ltd.) and jojoba seed oil (trade name: ECO OIL RS, Supplier: Kokyu Alcohol Kogyo Co., Ltd.) both having similar viscosity. It can be understood that the compounds of formula (I) exhibit excellent smoothness although they have fairly high viscosity.

In addition, TCDNP has a smoothness comparable to dimethicone.

Therefore, they can be used in a wide range of formulations such as skin care products, body care products, make-up products and hair care products.

Moreover, it can be understood that the ester compounds of formula (I) have smaller values of fluctuation of mean frictional coefficient (MMD), lower roughness, and better smoothness.

Therefore, they can be used in a wide range of formulations such as skin care products, body care products, make-up products and hair care products.

<Compatibility with Various Types of Oil Agent>

Each of TCDNP and TCDDNP obtained in Synthesis Examples 1 and 8 and each of oily bases are combined with a weight ratio of 9:1 or 1:1, and dissolved in a water bath at 80-90° C. for approximately 30 min with stirring, then cooled to 50° C. with stirring, and stored in a thermostatic chamber at 25° C. Their compatibility was evaluated by visually checking the state after 1 week. Results are shown in Table 3.

TABLE 3

Compatibility with various types of oils.

| | TCDNP | | TCDDNP | |
|---|---|---|---|---|
| Component | 10% | 50% | 10% | 50% |
| Ethanol | C | C | C | C |
| Glycerin | N | N | N | N |
| Squalane | C | C | C | C |
| Mineral oil | C | C | C | C |
| Hydrogenated polyisobutene | C | C | C | C |
| Isononyl isononanoate | C | C | — | — |
| Neopentyl glycol diethylhexanoate | C | C | — | — |
| Triethylhexanoin | — | — | C | C |
| Octyldodecanol | C | C | C | C |
| Polyglyceryl-2 triisostearate | C | C | C | C |
| Diisostearyl malate | C | C | — | — |
| Olive oil | — | — | C | C |
| Isostearic acid | — | — | C | C |
| Cyclomethicone | C | C | C | C |
| Dimethicone (10 mm²/s) | C | C | C | C |

C: Compatible
N: Not compatible
—: Not tested

As shown in Table 3, TCDNP and TCDDNP have excellent compatibility with the oil agents other than glycerin (trade name: TRIOL VE, Supplier: Kokyu Alcohol Kogyo Co., Ltd.). Therefore, selection of oils in the formulation design is easy, so that they can be used in a wide range of formulations such as skin care, make-up and hair care products.

<Ultraviolet Absorber Solubility>

Uvinul N 539 T (cosmetic ingredient labeling name: octocrylene, supplier: BASF Corporation) that is commonly used in cosmetic products, and Tinosorb S (cosmetic ingredient labeling name: bis ethylhexyl oxyphenol methoxyphenyl triazine, supplier: BASF Corporation) that is known as low-solubility ultraviolet absorber for which the type of oil agents dissolving is limited, were dissolved with each of oily bases at room temperature (25° C.) with stirring, and stored in a thermostatic chamber at 25° C. to determine the solubility. Their state after 1 week was evaluated visually. Results are shown in Table 4.

TABLE 4

Solubility of ultraviolet absorber.

| | Tinosorb S | | | Uvinul N 539 T | |
|---|---|---|---|---|---|
| Component | 2% | 5% | 7% | 5% | 20% |
| Isodecyl neopentanoate | C | N | — | — | C |
| Ethylhexyl isononanoate | C | N | — | — | — |
| Diisobutyl adipate | C | C | N | C | C |
| Isononyl isononanoate | C | N | — | — | C |
| Ethyl isostearate | C | N | — | — | C |
| Ethylhexyl succinate | C | C | N | — | — |
| Isotridecyl isononanoate | C | (N) | — | — | — |
| Neopentyl glycol diethylhexanoate | C | N | — | — | — |
| Isostearyl neopentanoate | C | N | — | — | C |
| Neopentyl glycol dicaprate | C | C | N | — | — |
| Neopentyl glycol diisononanoate | C | (N) | — | — | C |
| Ethylhexyl hydroxystearate | C | (N) | — | — | — |
| Octyldodecyl stearoyloxy stearate | N | — | — | — | — |
| Isopropyl dimerate | N | — | — | — | — |
| TCD ester of Synthesis Ex. 1 (TCDNP) | C | C | N | C | C |
| TCD ester of Synthesis Ex. 4 (TCDIN) | C | N | — | — | — |
| TCD ester of Synthesis Ex. 5 (TCDIS) | C | — | — | C | C |

C: Soluble
N: Insoluble
(N): Since it is insoluble when ultraviolet absorber is 3%, it is judged to be probably insoluble at 5% as well.
—: Not measured The compounds of formula (I) have a dissolving ability equivalent to that of diisobutyl adipate (trade name: KAK DIBA, Supplier: Kokyu Alcohol Kogyo Co., Ltd.) and diethylhexyl succinate (trade name: KAK DIOS, supplier: Kokyu Alcohol Kogyo Co., Ltd.), which are said to have high ultraviolet absorbers solubility as a component of cosmetic products. Therefore, the formulation design that uses ultraviolet absorbers becomes easy, enabling a wide range of formulations.

Example 1

Lipsticks with each of the following compositions shown in Table 5 were produced by a conventional method. Each component was mixed in a predetermined amount, dissolved at approximately 110° C. with stirring to obtain a uniform mixture. This mixture was cooled to approximately 30° C. to give lipsticks of Example 1 and Comparative Example 1. In Example 1, the ester compound obtained in Synthesis Example 1 (TCDNP) was used.

[Evaluation]

Physical properties of the lipsticks were determined as follows. Results are shown in Table 5.

<Storage Stability>

Paper was placed in the bottom of a given glass container, the lipstick was placed on it, and the container was stored in an incubator at 45° C. for 24 h. After storage, the lipstick alone was taken out; then the amount of the oil anent immersed in the paper due to sweating and the weight of the lipstick before storage were measured, and the sweating rate was calculated by the following formula and evaluated with three-grade evaluation.

Calculation formula: (Weight of oil absorbed to the paper/Weight of lipstick)×100=Sweating rate (%)

A: 0.5% or less (not sweating)
B: 0.5%-1.0% (some degree of sweating is confirmed, but there is no problem in practical use)
C: 1.0% or more (sweating is obviously confirmed, and there is a problem in practical use)

<Adhesion>

Artificial leather was placed on the sample stage of KES-SE Friction Tester (Kato Tech Co., Ltd.), and a lipstick was attached to the jig of the sensor and the tester was operated. One to three back-and-forth movements were carried out, and the amount of adhered amount was calculated as a difference in the weight of the artificial leather to which the lipstick was applied and the weight of the artificial leather before the operation. The average value of adhered amounts by one to three back-and-forth movements was evaluated according to the following evaluation criteria.

A: 5 mg or more (good adhesion)
B: 4-5 mg (moderate adhesion)
C: 4 mg or less (poor adhesion, unsuitable for practical use)

<Glossiness>

The sample was applied with a constant thickness and area on paraffin paper, and gloss levels were measured by Glossymeter GL200 (Courage+Khazaka electronic GmbH) (incident angle of 60°–reflection angle of 60°). An average value of three measurements was designated to be the gloss level, which was evaluated based on the following evaluation criteria.

A: Gloss level of 60 or more
B: Gloss level of 50-60
C: Gloss level of 50 or less

TABLE 5

Formulation and physical properties of transparent lipstick.

|  | Example 1 | Comp. Ex. 1 |
|---|---|---|
| Bisdialkyl(C14-18)amide (ethylenediamine/hydrogenated dimer dilinoleate) copolymer | 13.0 | 15.0 |
| Dibutyl lauroyl glutamide | 0.9 | 0.9 |
| Dibutyl ethylhexanoyl glutamide | 0.6 | 0.6 |
| Diisostearyl malate | 13.0 | 15.0 |
| Isotridecyl isononanoate | 52.0 | 68.5 |
| TCD ester of Synthesis Ex. 1 (TCDNP) | 20.5 | — |
| Storage stability | A | B |
| Adhesion | A | C |
| Glossiness | A | B |

As shown in Table 5, compared to the lipstick of Comparative Example 1, the lipstick of Example 1 is superior in storage stability and glossiness, and shows much higher adhesion.

The lipstick of Comparative Example 1 exhibits good smoothness, but its adhesion is not sufficient. The reason for this is as follows: in order to improve adhesion, concentration of the oil gelling agent (Sylvaclear A200V) must be decreased, but the decrease of the oil gelling agent leads to poor storage stability as a lip rouge (sweating is observed). On the other hand, in order to improve storage stability (to prevent sweating), the concentration of the oil-gelling agent must be increased, and accordingly adhesion is sacrificed.

Furthermore, since the gloss of lips weakens as the adhesion decreases, there is a problem in the shine (gloss) of lips after adherence.

To address this problem, by incorporating the compounds of formula (I), it is possible to decrease the concentration of the oil gelling agent (Sylvaclear A200V), thereby improving adhesion; in addition, storage stability and glossiness can be improved as well, even though the concentration of the oil gelling agent (Sylvaclear A200V) is decreased.

Examples 2-6

Using the ester compounds obtained in Synthesis Examples 2-5 and 8, lipsticks with a composition of the following Table 6 were produced in the same manner as in Example 1.

Physical properties were evaluated in the same manner as in Example 1. Results are shown in Table 7.

Comparative Example 2

Lipsticks without an ester compound having the composition of the following Table 6 were produced in the same manner as in Example 1.

Comparative Example A

Since the ester obtained in Synthesis Example A (TCD ester of formula (I) wherein R is a C1 alkyl group) was not appropriate for practical use due to its strong odor, evaluation of physical properties of this lipstick was not carried out.

TABLE 6

Formulation of lipstick.

|  | Comp. Ex. 2 | Example |
|---|---|---|
| Bisdialkyl(C14-18)amide (ethylenediamine/hydrogenated dimer dilinoleate)copolymer | 13.0 | 13.0 |
| Dibutyl lauroyl glutamide | 0.9 | 0.9 |
| Dibutyl ethylhexanoyl glutamide | 0.6 | 0.6 |
| Diisostearyl malate | 13.0 | 13.0 |
| Isotridecyl isononanoate | 72.5 | 52.0 |
| TCD ester compound |  | 20.5 |

Example 2: ester of Synthesis Example 2 (ester of n-pentanoic acid and TCD-Alcohol M)

Example 3: ester of Synthesis Example 3 (ester of isobutanoic acid and TCD-Alcohol M)

Example 4: ester of Synthesis Example 4 (ester of isononanoic acid and TCD-Alcohol M)

Example 5: ester of Synthesis Example 5 (ester of isostearic acid and TCD-Alcohol M)

Example 6: ester of Synthesis Example 8 (diester of neopentanoic acid and TCD-Alcohol DM)

TABLE 7

Formulation and physical properties of transparent lipstick.

| | Without TCD ester Comp. Ex. 2 | Number of carbons in fatty acid used for the synthesis of ester | | | | | |
|---|---|---|---|---|---|---|---|
| | | C4 Isobutanoic acid Example 3 | C5 n-pentanoic acid Example 2 | C5 Neopentanoic acid Example 1 | C9 Isononanoic acid Example 4 | C18 Isostearic acid Example 5 | C5 x 2 Dineopentanoic acid Example 6 |
| Storage stability | B | B | A | A | A | A | A |
| Adhesion | C | A | A | A | A | B | A |
| Glossiness | B | A | B | A | A | A | A |

We could confirm that any of the TCD esters of the present application could be practically used in cosmetic products. In addition, from the viewpoint of storage stability and adhesion, TCD esters having a fatty acid carbon number of 5-18 (TCD ester of formula (I) wherein R is a C4-C17 linear or branched alkyl group) are preferred. Furthermore, the ester of neopentanoic acid and TCD-Alcohol DM (di-ester) also showed good results.

Meanwhile, TCD esters of isobutanoic acid (TCD ester of formula (I) wherein R is a C3 branched alkyl group) have slight odor, but it is judged that they can be practically used in cosmetic products; and other TCD esters have no odor or only very weak odor, so that they are suitable for application to all cosmetic products.

Examples 7-9

The following oil agents were used in place of the base oil agent (isotridecyl isononanoate) in Example 1 and Comparative Example 2, and the effects of adding the TCD ester in various base oil agents were evaluated in the same manner as in Example 1. Results are shown in Table 8.

Comparative Example 6

In order to evaluate effects of the ester compounds, in place of TCDNP, an ester of lauryl alcohol and neopentanoic acid having the same carbon number was used to produce lipsticks in the same manner as in Example 1, and their physical properties were evaluated by comparison. Results are shown in Table 9.

TABLE 9

Formulation and physical properties of transparent lipstick.

| | Example 1 | Comp. Ex. 6 |
|---|---|---|
| (Bisdioctadecyl amide dimer dilinoleate/ethylenediamine) copolymer | 13.0 | 13.0 |
| Dibutyl lauroyl glutamide | 0.9 | 0.9 |
| Dibutyl ethylhexanoyl glutamide | 0.6 | 0.6 |
| Diisostearyl malate | 13.0 | 13.0 |
| Isotridecyl isononanoate | 52.0 | 52.0 |
| TCD ester of Synthesis Ex. 1 (TCDNP) | 20.5 | |
| Lauryl neopentanoate | | 20.5 |
| Storage stability | A | B |

TABLE 8

Effects of addition of TCD ester in terms of various base oils.

| | Comp. Ex. 2 | Example 1 | Comp. Ex. 3 | Example 7 | Comp. Ex. 4 | Example 8 | Comp. Ex. 5 | Example 9 |
|---|---|---|---|---|---|---|---|---|
| Bisdialkyl(C14-18)amide (ethylenediamine/hydrogenated dimer dilinoleate) copolymer | 13.0 | 13.0 | 13.0 | 13.0 | 13.0 | 13.0 | 13.0 | 13.0 |
| Dibutyl lauroyl glutamide | 0.9 | 0.9 | 0.9 | 0.9 | 0.9 | 0.9 | 0.9 | 0.9 |
| Dibutyl ethylhexanoyl glutamide | 0.6 | 0.6 | 0.6 | 0.6 | 0.6 | 0.6 | 0.6 | 0.6 |
| Diisostearyl malate | 13.0 | 13.0 | 13.0 | 13.0 | 13.0 | 13.0 | 13.0 | 13.0 |
| Isotridecyl isononanoate | 72.5 | 52.0 | | | | | | |
| Cetyl ethylhexanoate | | | 72.5 | 52.0 | | | | |
| Octyldodecyl miristate | | | | | 72.5 | 52.0 | | |
| Neopentyl glycol dicaprate | | | | | | | 72.5 | 52.0 |
| TCD ester of Synthesis Ex. 1 (TCDNP) | | 20.5 | | 20.5 | | 20.5 | | 20.5 |
| Storage stability | B | A | C | B | C | B | C | B |
| Adhesion | C | A | C | B | B | A | B | A |
| Gloss | B | A | C | A | B | A | B | A |

Diisostearyl malate (trade name: HAIMALATE DIS, Supplier: Kokyu Alcohol Kogyo Co., Ltd.)
Cetyl ethylhexanoate (trade name: CEH, Supplier: Kokyu Alcohol Kogyo Co., Ltd.)
Octyldodecyl myristate (trade name: ODM, Supplier: Kokyu Alcohol Kogyo Co., Ltd.)
Neopentyl glycol dicaprate (trade name: NPDC, Supplier: Kokyu Alcohol Kogyo Co., Ltd.)

In the cases where TCDNP is not blended, storage stability and adhesion in each base oil agents are poor; however, storage stability and adhesion are improved by blending TCDNP. Therefore, we can confirm that performance can be improved from conventional formulations by blending TCDNP, regardless of the kind of base oil agents.

TABLE 9-continued

Formulation and physical properties of transparent lipstick.

|  | Example 1 | Comp. Ex. 6 |
|---|---|---|
| Adhesion | A | B |
| Gloss | A | B |

From the results shown in Table 9, we were able to confirm that as compared to lauryl neopentanoate that is an ester having no cyclic structure, TCDNP having a cyclic structure could provide excellent storage stability, adhesion, and glossiness.

Example 10

Skin creams having the following composition shown in the table below were produced by a conventional method. Each component was mixed in a predetermined amount, and dissolved at approximately 90° C. with stirring to obtain a homogeneous mixture, giving skin creams of Example 10, Comparative Example 10A, and Comparative Example 10B.

TABLE 10

Formulation and physical properties of skin cream.

|  |  | Example 10 SC-1 | Comp. Ex. 10A SC-2 | Comp. Ex. 10B SC-3 |
|---|---|---|---|---|
| Oil phase | Mineral oil | 10.00 | 10.00 | 15.00 |
|  | TCDIN | 5.00 |  |  |
|  | KAK 109 (Isodecyl isononanoate) |  | 5.00 |  |
|  | Behenyl alcohol 65 | 4.00 | 4.00 | 4.00 |
|  | Polysorbate 80 | 2.00 | 2.00 | 2.00 |
| Aqueous phase | Diol PD | 3.00 | 3.00 | 3.00 |
|  | Triol VE | 2.00 | 2.00 | 2.00 |
|  | (Acryloyl dimethyl taurine ammonium/VP) copolymer | 0.22 | 0.22 | 0.22 |
|  | Xanthane gum | 0.08 | 0.08 | 0.08 |
|  | Purified water | 73.70 | 73.70 | 73.70 |
|  | Spreadability | A | A | B |
|  | Moisturized feeling | A | C | C |
|  | Storage stability | A | A | A |

[Evaluation]
Physical properties of the skin creams were determined as follows. Results are shown in Table 10.
<Spreadability/Moisturized Feeling>
"Spreadability" and "moisturized feeling" upon application to the skin were evaluated by ten sensory test panelists. Ambient temperature at the time of the sensory test is 25±5° C., and humidity is 50±10%.
In the evaluation, scoring was performed with the following five grades, and an average value of obtained scores was represented according the three-grade evaluation criteria.

TABLE 11

| Spreadability | Moisturized feeling |  |
|---|---|---|
| Heavy | Moisturized | 5 points |
| Slightly heavy | Slightly Moisturized | 4 points |
| Moderate | Moderate | 3 points |
| Slightly light | Slightly light | 2 points |
| Light | Light | 1 points |

TABLE 11-continued

| Spreadability | Moisturized feeling |
|---|---|

A: 4 points or more
B: 2-3 points
C: 1 point

<Storage Stability>
For evaluation, the following cycle test were carried out for five times: a formulation at room temperature was stored at 0° C., then the temperature was changed from 0° C. to room temperature, and the sample was stored at 40° C., then the temperature was changed from 40° C. to the room temperature; and the sample state was visually evaluated and judged by the following three-grade evaluation criteria.
A: No separation is observed
B: Separation is slightly observed
C: Separation is observed From the results shown in Table 10, we were able to confirm that, as compared to isodecyl isononanoate that is an ester having no cyclic structure, TCDIN having a cyclic structure could provide good spreadability and moisturized feeling, as well as excellent storage stability.

By using the ester compounds of the present invention, a skin cream having both good texture upon application (good spreadability) and good texture after use (moisturized feeling) was obtained.

Example 11

UV creams having the following composition shown in Table 12 were produced by a conventional method. Each component was mixed in a predetermined amount, and dissolved at approximately 90° C. with stirring to obtain a homogeneous mixture, giving the UV creams of Example 11 and Comparative Example 11.
The results of evaluating physical properties in the same manner as in Example 10 are shown in Table 12 below.

TABLE 12

Formulation and physical properties of UV cream.

|  |  | Example 11 UVC-1 | Comp. Ex. 11 UVC-2 |
|---|---|---|---|
| Oil phase | Ethylhexyl methoxycinnamate | 10.00 | 10.00 |
|  | Octocrylene | 8.00 | 8.00 |
|  | TCDNP | 7.00 |  |
|  | Lauryl neopentanoate |  | 7.00 |
|  | Glyceryl stearate (SE) | 4.00 | 4.00 |
|  | t-Butyl methoxydibenzoylmethane | 2.00 | 2.00 |
|  | Behenyl alcohol 65 | 0.20 | 0.20 |
| Aqueous phase | Diol PD | 3.00 | 3.00 |
|  | BG | 2.00 | 2.00 |
|  | (Acrylate/alkyl acrylate (C10-30)) crosspolymer | 0.15 | 0.15 |
|  | Sodium hydroxide | 0.06 | 0.06 |
|  | Purified water | 63.59 | 63.59 |
|  | Spreadability | A | B |
|  | Moisturized feeling | A | B |
|  | Storage stability | A | A |

We were able to confirm from the results in Table 12 that, in addition to good ability to dissolve an ultraviolet absorber octocrylene (trade name: Uvinul N 539 T, Supplier: BASF Corporation), TCDNP having a cyclic structure could provide good spreadability and moisturized feeling, as well as excellent storage stability, as compared to mineral oils that are common oil agents for cosmetic material, and lauryl neopentanoate that is an ester having no cyclic structure.

By using the ester compound of the present invention, a UV cream having both good texture upon application (good spreadability) and good texture after use (moisturized feeling) was obtained.

Example 12

Cosmetic oils having the composition shown in Table 13 below were produced by a conventional method. Each component was mixed in a predetermined amount, and dissolved at approximately 60° C. with stirring to obtain a homogeneous mixture, giving the cosmetic oils of Example 12A, Example 12B, and Comparative Example 12.

The results of evaluating physical properties in the same manner as in Example 10 are shown in Table 13.

TABLE 13

Formulation and physical properties of cosmetic oil.

|  | Example 12A SO-1 | Example 12B SO-2 | Comp. Ex. 12 SO-2 |
|---|---|---|---|
| Eco oil RS | 50.0 | 50.0 | 50.0 |
| Olive squalane | 25.0 | 25.0 | 25.0 |
| TCDIS | 15.0 | | |
| TCDDNP | | 15.0 | |
| ICIS (Hexyldecyl isostearate) | | | 15.0 |
| IPP | 9.9 | 9.9 | 9.9 |
| Tocopherol | 0.1 | 0.1 | 0.1 |
| Spreadability | A | A | A |
| Moisturized feeling | A | A | B |

From the results shown in Table 13, we were able to confirm that, as compared to hexyldecyl isostearate that is an ester having no cyclic structure, TCDIS and TCDDNP having a cyclic structure could provide good spreadability and moisturized feeling.

By using the ester compounds of the present invention, cosmetic oils having both good texture upon application (good spreadability) and good texture after use (moisturized feeling) can be obtained.

Example 13

Cleansing oils having the composition shown in Table 14 below were produced by a conventional method. Each component was mixed in a predetermined amount, and dissolved at approximately 60° C. with stirring to obtain a homogeneous mixture, giving the cleansing oils of Example 13, Comparative Example 13A, and Comparative Example 13B.

TABLE 14

Formulation and physical properties of cleansing oil.

|  | Example 13 CO-1 | Comp. Ex. 13A CO-2 | Comp. Ex. 13B CO-3 |
|---|---|---|---|
| Mineral oil | 50.0 | 50.0 | 90.0 |
| TCDIS | 40.0 | | |
| ICIS (Hexyldecyl isostearate) | | 40.0 | |
| PEG-30 glyceryl triisostearate | 7.0 | 7.0 | 7.0 |
| PEG-10 glyceryl diisostearate | 3.0 | 3.0 | 3.0 |
| Cleansing power | A | A | C |

TABLE 14-continued

Formulation and physical properties of cleansing oil.

|  | Example 13 CO-1 | Comp. Ex. 13A CO-2 | Comp. Ex. 13B CO-3 |
|---|---|---|---|
| Feeling after washing | A | B | B |

[Evaluation]

Physical properties of the cleansing oils were determined as follows. Results are shown in Table 14.

<Cleansing Power>

A commercially available lip rouge was applied to the constant area of an artificial leather, and it was left to dry for 2 hr; 0.5 g of each cleansing oil formulation was applied to the area, then the area was rubbed by lightly moving fingers for five back-and-forth movements, rinsed with warm water of approximately 40° C., and the condition of the remained lip rouge was visually observed.

A: Good compatibility of cleansing cosmetic material with a make-up product, and the make-up product is removed well.
B: Fair compatibility of cleansing cosmetic material with a make-up product, and the make-up product is removed fairly well.
C: Poor compatibility of cleansing cosmetic material with a make-up product, and the make-up product is not well removed.

<Feeling after Washing>

Ten sensory evaluation panelists evaluated the feeling after washing (dry feeling) of each of the cleansing formulations rinsed with warm water of approximately 40° C.

Three-grade evaluation was performed using the number of panelists who judged "good feeling after washing (=dry and non-tacky feeling)".
A: 7 or more panelists
B: 4-6 panelists
C: 3 panelists or less From the results shown in Table 14, we were able to confirm that, as compared to mineral oil that is common oil agent and hexyldecyl isostearate that is an ester having no cyclic structure, TCDIS that is an ester having a cyclic structure could provide excellent cleansing power and feeling after washing.

By using the ester compound of the present invention, cleansing agents having both excellent function (cleansing power) and excellent feeling of use (feeling after washing) can be obtained.

Examples 14 and 15

Hair oils having the composition shown in Table 15 below were produced by a conventional method. Each component was mixed in a predetermined amount, and dissolved at approximately 60° C. with stirring to obtain a homogeneous mixture, giving the hair oils of Example 14, Comparative Example 14A, and Comparative Example 14B.

TABLE 15

Formulation and physical properties of hair oil.

|  | Example 14 HO-1 | Comp. Ex. 14A HO-2 | Comp. Ex. 14B HO-3 |
|---|---|---|---|

TABLE 15-continued

[Formulation and physical properties of hair oil.]

| | | | |
|---|---|---|---|
| Mineral oil | 45.0 | 45.0 | 65.0 |
| Cyclopentasiloxane | 30.0 | 30.0 | 30.0 |
| TCDNP | 20.0 | | |
| Lauryl neopentanoate | | 20.0 | |
| Ethylhexyl methoxycinnamate | 5.0 | 5.0 | 5.0 |
| Tackiness upon application | A | B | C |
| Finger combability (no roughness) | A | A | B |
| Hair manageability | A | B | B |

| | Example 15 HO-4 | Comp. Ex. 15A HO-5 | Comp. Ex. 15B HO-3 |
|---|---|---|---|
| Mineral oil | 45.0 | 45.0 | 65.0 |
| Cyclopentasiloxane | 30.0 | 30.0 | 30.0 |
| TCDIN | 20.0 | | |
| KAK 109 (Isodecyl isononanoate) | | 20.0 | |
| Ethylhexyl methoxycinnamate | 5.0 | 5.0 | 5.0 |
| Tackiness upon application | A | B | C |
| Finger combability (no roughness) | A | B | B |
| Hair manageability | B | C | B |

[Evaluation] (Evaluation on Hair)

Physical properties of hair oils were determined as follows. Results are shown in Table 15.

<Tackiness Upon Application>

Ten sensory evaluation panelists evaluated the feeling after application of each hair oil formulation to their hair.

Three-grade evaluation was performed using the number of panelists who judged that "no tackiness after application."
A: 7 or more panelists
B: 4-6 panelists
C: 3 panelists or less <Finger Combability (No Roughness)>

Human hair bundles BS-B3N (100% black hair, aligned at the roots II, Beaulax, Co., Ltd.) were subjected to damage treatment by our pre-determined method, then to the damaged hair, approximately 2 mL of each hair oil was dropped and applied evenly using a spatula; the resulting hair samples were measured by KES-SE Friction Tester (Kato Tech Co., Ltd.).

An average of the obtained values of MMD (n=3) was calculated, and the obtained average value was evaluated in accordance with the following three-grade evaluation criteria. *MMD: MMD is a fluctuation of mean frictional coefficient, and a smaller MMD indicates smaller fluctuation of a fluctuation of mean frictional coefficient, i.e. reduced roughness and better finger-combing smoothness.
A: 0.003 or less
B: 0.003-0.005
C: 0.005 or more <Hair Manageability>

Ten sensory evaluation panelists evaluated hair manageability after application of each hair oil to their hair.

Three-grade evaluation was performed using the number of panelists who judged that "hair manageability is good (=no tackiness after application and frizzing of the hair is suppressed)".
A: 7 or more panelists
B: 4-6 panelists
C: 3 panelists or less From the results shown in Table 15, we were able to confirm that, as compared to mineral oil that is common oil agent and lauryl neopentanoate or isodecyl isononanoate that are esters having no cyclic structure, TCDNP or TCDIN which has a cyclic structure could provide non-tackiness upon application, good finger combability (no roughness), and good hair manageability.

By using the ester compounds of the present invention, hair oils having both excellent texture at the time of use such as non-tackiness upon application and good finger combability (no roughness), and excellent texture after use such as good hair manageability, can be obtained.

In the following, formulation examples of cosmetic products such as make-up products, skin care products and hair care products using TCD esters are shown.

<Make-Up Products>

TABLE 16

[Lipstick formulation 1]

| | |
|---|---|
| (Polyglyceryl-2 isostearate/dimer dilinoleate) copolymer | 5.00 |
| Hydrogenated polyisobutene | 5.00 |
| Hydrogenated castor oil dimer dilinoleate | 10.00 |
| Polyglyceryl-2 triisostearate | 6.00 |
| Diisostearyl malate | 10.00 |
| Caprylic/capric triglyceride | 20.00 |
| TCD ester | 15.00 |
| Squalane | 1.00 |
| Octyldodecanol | 5.00 |
| Candelilla wax | 3.00 |
| Ceresin | 5.00 |
| Polyethylene | 5.00 |
| Microcrystalline wax | 3.00 |
| Red No. 201 | 1.40 |
| Red No. 202 | 1.10 |
| Colcothar | 1.20 |
| Titanium oxide | 0.80 |
| Titanium dioxide-coated mica [Pearl pigment] | 2.50 |
| | 100.00 |

TABLE 17

[Lipstick formulation 2]

| | |
|---|---|
| Hydrogenated polyisobutene | 10.00 |
| Hexa(hydroxystearic acid/stearic acid/rosin acid) dipentaerythrityl | 5.00 |
| Hydrogenated castor oil isostearate | 5.00 |
| Polyglyceryl-2 isostearate | 10.00 |
| Diisostearyl malate | 10.00 |
| Pentaerythrityl tetraisostearate | 10.00 |
| Triethylhexanoin | 10.00 |
| Ethylhexyl hydroxystearate | 8.00 |
| TCD ester | 10.00 |
| Dextrin palmitate | 1.70 |
| Beeswax | 3.00 |
| Polyethylene | 5.00 |
| Synthetic wax, (ethylene/propylene) copolymer | 1.00 |
| Microcrystalline wax | 4.00 |
| Colcothar | 0.40 |
| Red No. 226 [CI 73360] | 1.60 |
| Titanium oxide | 1.00 |
| Titanium dioxide-coated mica [Pearl pigment] | 4.00 |
| Synthetic phlogopite, Titanium oxide, Iron oxide [Lame agent] | 0.30 |
| | 100.00 |

TABLE 18

[Lipstick formulation 3]

| | |
|---|---|
| Dipentaerythrityl hexaisononanoate | 25.10 |
| Caprylic/capric triglyceride | 22.50 |
| Hydrogenated castor oil dimer dilinoleate | 12.10 |
| TCD ester | 5.00 |
| Diisostearyl malate | 9.00 |
| Polyglyceryl-2 triisostearate | 4.50 |
| Microcrystalline wax | 4.50 |
| Ceresin | 3.60 |
| Polyethylene | 2.70 |

TABLE 18-continued

[Lipstick formulation 3]

| | |
|---|---|
| Candelilla wax | 0.90 |
| Pink-color formulated lake 1 | 10.00 |
| Tocopherol | 0.10 |
| | 100.00 |

TABLE 19

[Lip gloss formulation 1]

| | |
|---|---|
| (Polyglyceryl-2 isostearate/dimer dilinoleate) copolymer | 20.00 |
| Polybutene | 15.00 |
| Diisostearyl malate | 14.00 |
| Pentaerythrityl Tetra isostearate | 10.00 |
| Octyldodecyl stearoyloxy stearate | 10.00 |
| Hydrogenated castor oil dimer dilinoleate | 5.00 |
| (Diglycerin/dilinoleic acid/hydroxy stearic acid) copolymer | 5.00 |
| Polyglyceryl-2 isostearate | 5.00 |
| Polyglyceryl-2 triisostearate | 5.00 |
| Octyldodecanol | 2.50 |
| TCD ester | 2.00 |
| Inulin stearate | 2.00 |
| Di-(C20-40)-alkyl dimer dilinoleate | 2.00 |
| Dextrin palmitate/ethylhexanoate | 2.00 |
| Synthetic phlogopite, Titanium oxide, Iron oxide [Lame agent] | 0.30 |
| Titanium oxide | 0.15 |
| Red 202 [CI 15850] | 0.03 |
| Red 201 [CI 15850] | 0.02 |
| | 100.00 |

TABLE 20

[Lip gloss formulation 2]

| | |
|---|---|
| (Polyglyceryl-2 isostearate/dimer dilinoleate) copolymer | 30.00 |
| Mineral oil | 23.00 |
| Hydrogenated polyisobutene | 20.00 |
| TCD ester | 19.50 |
| Microcrystalline wax | 2.00 |
| Silica dimethyl silylate [AEROSIL ® R 972] | 2.00 |
| Titanium dioxide-coated mica [Pearl pigment] | 2.00 |
| 12-hydroxy stearic acid | 0.50 |
| Polyethylene | 0.50 |
| Borosilicate (Ca/Al), Silica, Titanium oxide, Tin oxide [Lame agent] | 0.50 |
| | 100.00 |

Since TCD esters are highly compatible with various oil agents, they can also be blended in the formulation to which various kinds of oil agents are blended, such as lip gloss, and improve gloss and adhesion.

(Polyglyceryl-2 isostearate/dimer dilinoleate) copolymer (trade name: HAILUCENT ISDA, Supplier: Kokyu Alcohol Kogyo Co., Ltd.)

Hydrogenated castor oil dimer dilinoleate (trade name: RISOCAST DA-L, Supplier: Kokyu Alcohol Kogyo Co., Ltd.)

Dipentaerythrityl hexaisononanoate (trade name: HAILUCENT DPIN6, Supplier: Kokyu Alcohol Kogyo Co., Ltd.)

TABLE 21

[Foundation formulation]

| | | |
|---|---|---|
| [Oil phase] | Cyclomethicone | 15.00 |
| | Titanium oxide | 7.00 |

TABLE 21-continued

[Foundation formulation]

| | | |
|---|---|---|
| | Neopentyl glycol diethylhexanoate | 5.00 |
| | TCD ester | 5.00 |
| | Microcrystalline wax | 4.00 |
| | Dimethicone | 2.00 |
| | Pentylene glycol | 2.00 |
| | Cetanol | 2.00 |
| | Dextrin palmitate | 2.00 |
| | Cross-linked silicone end | 2.00 |
| | Talc | 1.35 |
| | Yellow oxide of iron | 1.20 |
| | Dimethicone copolyol | 1.20 |
| | Ethylhexyl methoxycinnamate | 1.00 |
| | Cetostearyl alcohol | 1.00 |
| | (Polyglyceryl-2 isostearate/dimer dilinoleate) copolymer | 0.50 |
| | Hydrogenated rape seed oil alcohol | 0.50 |
| | Red oxide of iron | 0.30 |
| | Black oxide of iron | 0.15 |
| [Aqueous phase] | Glycerin | 3.00 |
| | Hydroxyethyl cellulose | 0.30 |
| | Preservative | Adequate amount |
| | Water | 43.50 |
| | | 100.00 |

Since TCD esters are highly compatible with various oil agents and dissolve UV absorbers, they can be utilized in foundations.

TABLE 22

[Eyeshadow formulation]

| | | |
|---|---|---|
| [Oil phase] | Hydrophobized ultramarine | 8.20 |
| | Neopentyl glycol diethylhexanoate | 5.00 |
| | Diisostearyl malate | 5.00 |
| | Cyclomethicone | 5.00 |
| | TCD ester | 3.00 |
| | Dextrin palmitate | 3.00 |
| | (Polyglyceryl-2 isostearate/dimer dilinoleate) copolymer | 2.50 |
| | Mineral oil | 2.00 |
| | Glyceryl stearate (SE) | 1.50 |
| | Black oxide of iron | 1.10 |
| | Polyglyceryl-10 stearate | 1.00 |
| | Titanium dioxide-coated mica | 1.00 |
| [Aqueous phase] | Pentylene glycol | 3.00 |
| | Glycerin | 2.00 |
| | BG | 2.00 |
| | Preservative | Adequate amount |
| | Water | 62.90 |
| | | 100.00 |

Since TCD esters are highly compatible with various oil agents, they can be utilized in eyeshadows.

<Skin Care Products>

TABLE 23

[Cleansing oil formulation]

| | |
|---|---|
| Mineral oil | 45.00 |
| TCD ester | 15.00 |
| PEG-30 glyceryl triisostearate | 15.00 |
| Hexyldecyl ethylhexanoate | 10.00 |
| Jojoba seed oil | 5.00 |
| Polyglyceryl-2 triisostearate | 5.00 |
| PEG-10 glyceryl diisostearate | 5.00 |
| | 100.00 |

TABLE 24

[Cleansing cream formulation]

| | | |
|---|---|---|
| [Oil phase] | TCD ester | 25.00 |
| | Mineral oil | 25.00 |
| | Hydrogenated rape seed oil alcohol | 3.00 |
| | PEG-5 glyceryl triisostearate | 3.00 |
| | PEG-30 glyceryl triisostearate | 2.00 |
| | Polyglyceryl-1 stearate | 1.00 |
| [Aqueous phase] | Glycerin | 0.20 |
| | Sodium stearoyl glutamate | 0.10 |
| | (Acryloyl dimethyl taurine ammonium/VP) copolymer | 0.10 |
| | Water | 40.60 |
| | | 100.00 |

Since TCD esters are highly compatible with various oil agents, they can be utilized in cleansing cosmetic materials.

TABLE 25

[Skin lotion formulation]

| | | |
|---|---|---|
| [Oil phase] | Glycerin | 3.00 |
| | PEG-50 hydrogenated castor oil triisostearate/ PEG-60 hydrogenated castor oil | 2.00 |
| | Phytosteryl/behenyl/octyldodecyl lauroyl glutamate | 0.50 |
| | TCD ester | 0.30 |
| | Ethylhexyl methoxycinnamate | 0.15 |
| | Tocopherol acetate | 0.10 |
| | Butylparaben | 0.10 |
| [Aqueous phase] | BG | 5.00 |
| | Methylparaben | 0.20 |
| | Water | 88.65 |
| | | 100.00 |

TABLE 26

[Skin cream formulation]

| | | |
|---|---|---|
| [Oil phase] | TCD ester | 4.00 |
| | Squalane | 4.00 |
| | Pentylene glycol | 3.00 |
| | (Polyglyceryl-2 isostearate/dimer dilinoleate) copolymer | 2.00 |
| | Hexyldecyl isostearate | 2.00 |
| | Cetearyl alcohol | 2.00 |
| | Polyglyceryl-10 stearate | 1.50 |
| | Behenyl alcohol | 1.00 |
| [Aqueous phase] | Glycerin | 2.00 |
| | (Acryloyl dimethyl taurine ammonium/VP) copolymer | 0.22 |
| | Xanthane gum | 0.08 |
| | Water | 78.20 |
| | | 100.00 |

TABLE 27

[UV cream formulation]

| | | |
|---|---|---|
| [Oil phase] | Ethylhexyl methoxycinnamate | 10.00 |
| | Octocrylene | 8.00 |
| | TCD ester | 6.00 |
| | Glyceryl stearate (SE) | 4.00 |
| | t-Butyl methoxydibenzoylmethane | 2.00 |
| | Jojoba seed oil | 1.00 |
| | Behenyl alcohol | 0.20 |
| [Aqueous phase] | Pentylene glycol | 3.00 |
| | BG | 2.00 |
| | (Acrylate/alkyl acrylate (C10-30)) crosspolymer | 0.15 |
| | Sodium hydroxide | 0.06 |
| | Water | 63.59 |

TABLE 27-continued

[UV cream formulation]

| | |
|---|---|
| | 100.00 |

Since TCD esters are highly compatible with various oil agents and soluble in UV absorbers, they can be utilized in UV cosmetic materials.

TABLE 28

[Cosmetic oil (skin oil) formulation]

| | |
|---|---|
| Jojoba seed oil | 50.00 |
| Squalane | 25.00 |
| TCD ester | 14.90 |
| Isopropyl palmitate | 10.00 |
| Tocopherol | 0.10 |
| | 100.00 |

Since TCD esters are highly compatible with various oil agents, they can be utilized in cosmetic oils wherein vegetable oils are blended.

<Hair Care Products>

TABLE 29

[Hair mist formulation 1]

| | |
|---|---|
| Ethanol | 7.00 |
| TCD ester | 2.00 |
| Steartrimonium chloride | 2.00 |
| Behentrimonium chloride | 1.50 |
| Dimethicone | 0.50 |
| Water | 87.00 |
| | 100.00 |

TABLE 30

[Hair mist formulation 2]

| | |
|---|---|
| Ethanol | 15.00 |
| Bis-ethoxydiglycol succinate | 7.50 |
| TCD ester | 3.00 |
| Pentylene glycol | 3.00 |
| Steartrimonium chloride | 1.00 |
| Sodium citrate | 0.18 |
| Citric acid | 0.02 |
| Water | 70.30 |
| | 100.00 |

Since TCD esters are highly compatible with various oil agents, they can be utilized in hair mists wherein ethanol is blended.

TABLE 31

[Hair treatment formulation 1]

| | | |
|---|---|---|
| [Oil phase] | Behenyl alcohol | 5.50 |
| | Stearyl alcohol | 4.00 |
| | TCD ester | 3.00 |
| | Behentrimonium chloride | 3.00 |
| | Steartrimonium chloride | 2.00 |
| | Stearyl stearate | 2.00 |
| | Sodium isostearoyl lactate | 2.00 |
| | Ceteth-40 | 0.50 |
| [Aqueous | Citric acid | 0.10 |

TABLE 31-continued

| [Hair treatment formulation 1] | | |
|---|---|---|
| phase] | Methylparaben | 0.10 |
| | Water | 77.80 |
| | | 100.00 |

TABLE 32

| [Hair treatment formulation 2] | | |
|---|---|---|
| [Oil phase] | Cetearyl alcohol | 5.00 |
| | Hydrogenated castor oil isostearate | 3.00 |
| | Steartrimonium chloride | 3.00 |
| | DPG | 2.00 |
| | TCD ester | 1.50 |
| [Aqueous phase] | Pentylene glycol | 3.00 |
| | Hydroxyethyl cellulose | 0.30 |
| | Water | 82.20 |
| | | 100.00 |

Since TCD esters are highly compatible with various oil agents, they can be utilized in hair treatments.

TABLE 33

| [Hair oil formulation] | |
|---|---|
| Isostearyl isostearate | 35.00 |
| Isododecane | 22.00 |
| Triisostearine | 10.00 |
| Ethanol | 10.00 |
| TCD ester | 8.00 |
| Camellia oil | 6.00 |
| Dipentaerythrityl hexaisononanoate | 6.00 |
| Ethylhexyl methoxycinnamate | 3.00 |
| | 100.00 |

Since TCD esters are highly compatible with various oil agents, they can be utilized in hair oils wherein vegetable oils or silicone oils are blended.

INDUSTRIAL APPLICABILITY

As stated above, the compounds of formula (I) can be used in various cosmetic formulations.

The invention claimed is:
1. A compound of formula (Ia-3):

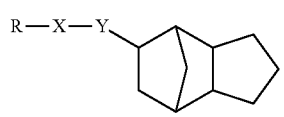

wherein:
R is a C8-C22 linear or branched alkyl group,
X is —CO—O— or —O—CO—, and
Y is a single bond or —CH$_2$.
2. 3,8-Bis-(neopentanoyloxymethyl)-tricyclo[5.2.1.0$^{2,6}$]decane.
3. A mixture comprising a non-fragrant cosmetic material comprising a compound of formula (I):

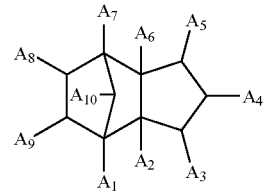

wherein:
A$_1$-A$_{10}$ are, each independently of one another, H or R—X—Y—,
wherein:
R is a C8-C22 linear or branched alkyl group,
X is —CO—O— or —O—CO—,
Y is a single bond or —CH$_2$—,
at least one of A$_1$-A$_{10}$ is R—X—Y—, and
when a plurality of R—X—Y— are present, each of R, X, and Y is independently selected; and
other components of cosmetic material that are not compounds of formula (I).
4. A non-fragrant cosmetic material comprising a compound of formula (Ia-1):

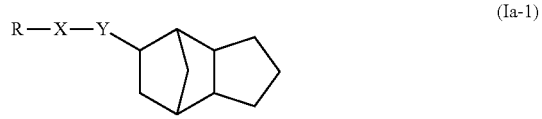

wherein:
R is a C8-C22 linear or branched alkyl group,
X is —CO—O— or —O—CO—, and
Y is —CH$_2$—.
5. A mixture comprising a cosmetic material comprising a compound of formula (Ia-2):

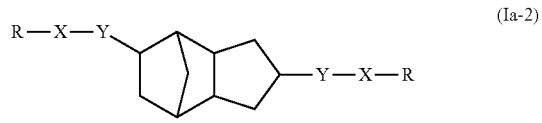

wherein:
R is a C3-C22 linear or branched alkyl group,
X is —CO—O— or —O—CO—,
Y is a single bond or —CH$_2$—, wherein
each of R, X and Y is independently selected; and
other components of cosmetic material that are not compounds of formula (Ia-2).
6. A cosmetic product comprising the mixture comprising a non-fragrant cosmetic material according to claim 3.
7. The cosmetic product according to claim 6, which is a lip rouge or lip gloss.
8. A mixture comprising an non-fragrant agent for improving feeling of use of cosmetic products, comprising a compound of formula (I):

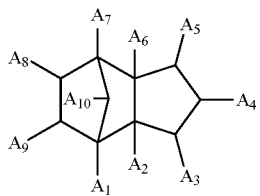

(I)

wherein:
A$_1$-A$_{10}$ are, each independently of one another, H or R—X—Y—,
wherein:
R is a C8-C22 linear or branched alkyl group,
X is —CO—O— or —O—CO—,
Y is a single bond or —CH$_2$—,
at least one of A$_1$-A$_{10}$ is R—X—Y—, and
when a plurality of R—X—Y— are present, each of R, X, and Y is independently selected; and
other components of cosmetic material that are not compounds of formula (I).

9. The mixture comprising a non-fragrant agent for improving feeling of use of cosmetic products according to claim 8, wherein the compound of formula (I) is a compound of formula (Ia):

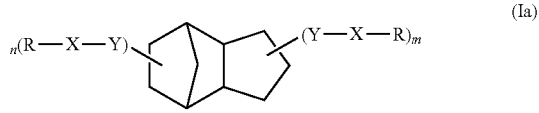

(Ia)

wherein:
n and m are, each independently, 0, 1 or 2,
n+m is 1, 2 or 3,
R is a C8-C22 linear or branched alkyl group,
X is —CO—O— or —O—CO—,
Y is a single bond or —CH$_2$—, and
when a plurality of R—X—Y— are present, each of R, X, and Y is independently selected.

10. A non-fragrant agent for improving feeling of use of cosmetic products comprising a compound of formula (Ia-1):

(Ia-1)

wherein:
R is a C8-C22 linear or branched alkyl group,
X is —CO—O— or —O—CO—, and
Y is —CH$_2$—.

11. A mixture comprising an agent for improving feeling of use of cosmetic products comprising a compound of formula (Ia-2):

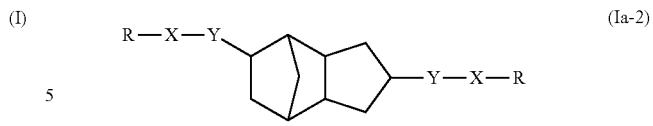

(Ia-2)

wherein:
R is a C3-C22 linear or branched alkyl group,
X is —CO—O— or —O—CO—,
Y is a single bond or —CH$_2$—, and
each of R, X, and Y is independently selected; and other components of cosmetic material that are not compounds of formula (Ia-2).

12. The non-fragrant agent for improving feeling of use according to claim 10, wherein the cosmetic product is a hair care product, a skin care product, a body care product and/or a make-up product.

13. The non-fragrant agent for improving feeling of use according to claim 12, wherein the skin care product is a cleansing product.

14. A non-fragrant cosmetic product comprising a compound of formula (I):

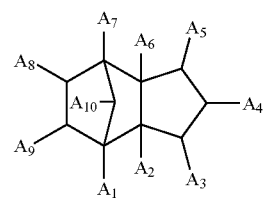

(I)

wherein:
A$_1$-A$_{10}$ are, each independently of one another, H or R—X—Y—,
wherein:
R is a C8-C22 linear or branched alkyl group,
X is —CO—O— or —O—CO—,
Y is a single bond or —CH$_2$—,
at least one of A$_1$-A$_{10}$ is R—X—Y—, and
when a plurality of R—X—Y— are present, each of R, X, and Y is independently selected.

15. The non-fragrant cosmetic product according to claim 14, which is selected from the group consisting of make-up products, hair care products, skin care products, and body care products.

16. A method for improving feeling of use of a non-fragrant cosmetic product comprising adding to the cosmetic product a compound of formula (I):

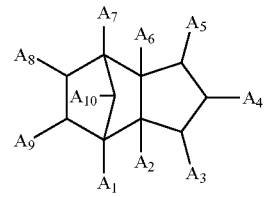

(I)

wherein:
A$_1$-A$_{10}$ are, each independently of one another, H or R—X—Y—, wherein:
R is a C8-C22 linear or branched alkyl group,
X is —CO—O— or —O—CO—,
Y is a single bond or —CH$_2$—,
at least one of $A_1$-$A_{10}$ is R—X—Y—, and
when a plurality of R—X—Y— are present, each of R, X, and Y is independently selected.

17. A method for improving feeling of use of a non-fragrant cosmetic product comprising adding to the cosmetic product a cosmetic material comprising a compound of formula (I):

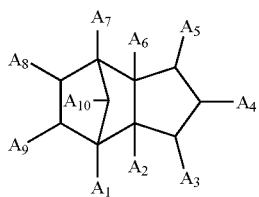

wherein:
$A_1$-$A_{10}$ are, each independently of one another, H or R—X—Y—,
wherein:
R is a C8-C22 linear or branched alkyl group,
X is —CO—O— or —O—CO—,
Y is a single bond or —CH$_2$—,
at least one of $A_1$-$A_{10}$ is R—X—Y—, and
when a plurality of R—X—Y— are present, each of R, X, and Y is independently selected.

18. A cosmetic product comprising the non-fragrant cosmetic material according to claim 4.

19. A cosmetic product comprising a compound of formula (Ia-2):

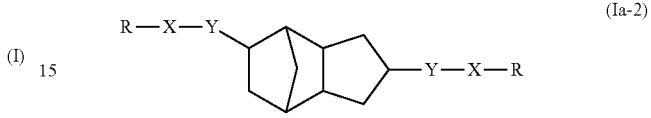

wherein:
R is a C3-C22 linear or branched alkyl group,
X is —CO—O— or —O—CO—,
Y is a single bond or —CH$_2$—, wherein
each of R, X and Y is independently selected.

20. The cosmetic product according to claim 6, wherein the cosmetic material is the base material for the cosmetic product.

* * * * *

UNITED STATES PATENT AND TRADEMARK OFFICE
CERTIFICATE OF CORRECTION

PATENT NO.       : 10,010,493 B2
APPLICATION NO.  : 15/112462
DATED            : July 3, 2018
INVENTOR(S)      : Mari Masuno et al.

Page 1 of 1

It is certified that error appears in the above-identified patent and that said Letters Patent is hereby corrected as shown below:

On the Title Page

Item [72], should read:
Mari Masuno, Narita-shi (JP); Kiyotaka Kawai, Narita-shi (JP)

Signed and Sealed this
Twelfth Day of November, 2019

Andrei Iancu
*Director of the United States Patent and Trademark Office*

UNITED STATES PATENT AND TRADEMARK OFFICE
CERTIFICATE OF CORRECTION

PATENT NO. : 10,010,493 B2
APPLICATION NO. : 15/112462
DATED : July 3, 2018
INVENTOR(S) : Mari Masuno et al.

Page 1 of 1

It is certified that error appears in the above-identified patent and that said Letters Patent is hereby corrected as shown below:

In the Claims

In Claim 1, at Column 35, Line 53, the text:
"(Ia-1)"
Should be replaced with:
-- (Ia-3) --.

Signed and Sealed this
Twenty-sixth Day of May, 2020

Andrei Iancu
*Director of the United States Patent and Trademark Office*